US010327940B2

(12) United States Patent
Summit et al.

(10) Patent No.: US 10,327,940 B2
(45) Date of Patent: Jun. 25, 2019

(54) SPIRAL BRACE

(71) Applicant: 3D Systems, Inc., Rock Hill, SC (US)

(72) Inventors: Scott Summit, Mill Valley, CA (US); Kenneth B Trauner, San Francisco, CA (US)

(73) Assignee: 3D SYSTEMS, INC., Rock Hill, SC (US)

( * ) Notice: Subject to any disclaimer, the term of this patent is extended or adjusted under 35 U.S.C. 154(b) by 399 days.

(21) Appl. No.: 14/846,631

(22) Filed: Sep. 4, 2015

(65) Prior Publication Data

US 2015/0374529 A1   Dec. 31, 2015

Related U.S. Application Data

(63) Continuation-in-part of application No. 14/255,801, filed on Apr. 17, 2014, and a continuation-in-part of application No. 13/791,678, filed on Mar. 8, 2013, now abandoned, which is a continuation-in-part of application No. PCT/US2012/051612, filed on Aug. 20, 2012, said application No. 14/255,801 is a continuation-in-part of application No. 13/214,096, filed on Aug. 19, 2011, now abandoned, said application No. PCT/US2012/051612 is a continuation-in-part of application No. 13/214,096, filed on Aug. 19, 2011, which is a continuation-in-part of application No. 12/820,968, filed on Jun. 22, 2010, now abandoned, which is a
(Continued)

(51) Int. Cl.
*A61F 5/00* (2006.01)
*A61F 5/01* (2006.01)

(52) U.S. Cl.
CPC .................................. *A61F 5/0118* (2013.01)

(58) Field of Classification Search
CPC .... A61F 5/0102; A61F 5/0118; A61F 5/0104; A61F 5/04; A61F 13/10; A61F 5/01; A61F 5/013; A61F 5/05858; A61F 5/05841; A61F 5/058; A61F 5/05866; A61F 13/107; A61F 13/104; A61F 5/00
See application file for complete search history.

(56) References Cited

U.S. PATENT DOCUMENTS 3,529,601 A   9/1970   Kirkland
3,680,549 A   8/1972   Lehneis et al.
(Continued)

FOREIGN PATENT DOCUMENTS

DE   20315822      1/2004
JP   H06-319791    11/1994
JP   2015-508075    4/2012

OTHER PUBLICATIONS

PCT International Search Report for International Application No. PCT/US13/66970, dated Jan. 17, 2014 (3 pages).
(Continued)

*Primary Examiner* — Victoria J Hicks
(74) *Attorney, Agent, or Firm* — Staniford Tomita LLP

(57) ABSTRACT

A spiral brace has an inner surface that corresponds to a digital representation of an injured limb. The spiral brace can wrap around a length of the limb in a helical manner. The body of the spiral brace may be a single piece structure that is fenestrated to provide air circulation to the injured limb.

20 Claims, 16 Drawing Sheets

Related U.S. Application Data continuation-in-part of application No. 12/615,196, filed on Nov. 9, 2009, now Pat. No. 8,005,651.

(60) Provisional application No. 61/720,861, filed on Oct. 31, 2012, provisional application No. 61/185,781, filed on Jun. 10, 2009, provisional application No. 61/168,183, filed on Apr. 9, 2009, provisional application No. 61/112,751, filed on Nov. 9, 2008.

(56) References Cited

U.S. PATENT DOCUMENTS

| | | | |
|---|---|---|---|
| 4,898,160 A | 2/1990 | Brownlee | |
| 5,409,451 A * | 4/1995 | Daneman | A61F 5/05866 |
| | | | 602/20 |
| 5,695,452 A | 12/1997 | Grim | |
| 5,713,836 A * | 2/1998 | O'keefe | A61F 5/05858 |
| | | | 602/20 |
| 5,911,126 A | 6/1999 | Massen | |
| 5,971,945 A * | 10/1999 | Garris | A61F 5/05866 |
| | | | 602/21 |
| 6,142,965 A | 11/2000 | Mathewson | |
| 6,267,743 B1 | 7/2001 | Bodenschatz et al. | |
| 6,783,507 B1 * | 8/2004 | Fisher | A61F 5/0118 |
| | | | 602/21 |
| 6,899,689 B1 | 5/2005 | Modglin | |
| 6,968,246 B2 | 11/2005 | Watson | |
| 7,033,330 B2 * | 4/2006 | de Lint | A61F 5/013 |
| | | | 602/16 |
| 7,037,286 B1 * | 5/2006 | Reinhardt | A61F 5/0118 |
| | | | 128/878 |
| 7,797,072 B2 | 9/2010 | Summit | |
| 2002/0068890 A1 | 6/2002 | Schwenn | |
| 2004/0121683 A1 | 6/2004 | Jordan et al. | |
| 2005/0015172 A1 | 1/2005 | Fried | |
| 2005/0054960 A1 | 3/2005 | Telles | |
| 2006/0140463 A1 | 6/2006 | Rutschmann | |
| 2006/0161267 A1 * | 7/2006 | Clausen | A61F 2/5046 |
| | | | 623/55 |
| 2007/0016323 A1 | 1/2007 | Fried | |
| 2009/0306801 A1 | 12/2009 | Sivak | |
| 2010/0138193 A1 | 6/2010 | Summit et al. | |
| 2010/0262054 A1 | 10/2010 | Summit et al. | |
| 2011/0301520 A1 | 8/2011 | Summit et al. | |
| 2012/0215146 A1 * | 8/2012 | Dao | A61F 5/0118 |
| | | | 602/20 |

OTHER PUBLICATIONS

PCT Written Opinion of the International Searching Authority for International Application No. PCT/US13/66970, dated Jan. 17, 2014 (7 pages).

Extended European Search Report for European Patent Application No. 13850056.6 dated Jun. 10, 2016 (7 pages).

Japanese Office Action for Japanese Application No. 2015-539872; dated Mar. 8, 2016 (2 pages).

D. Fortin et al., "A 3D Visulatization tool for the design and customization of spinal braces," 2007, Computerized Medical Imaging and Graphics, vol. 31, pp. 614-624.

Alyssa Q. Caddle et al., "Design of Patient-Specific Ankle-Foot Orthotics," Nov. 5, 2007, Northeastern University, 149 pages.

F. Bemajdoub et al., "Computer aided design of scoliosis braces," 1992, 14th Annual International Conference of the IEEE Engineering in Biology Society, pp. 2068-2069.

P. Abellard et al., "Developpement d'une methode de reconstruction 3D du tronc d'un scoliotique par imagerie stereoscopique," 1993, GRETSI, Group d'Etudes du Traitement du Signal et des images, pp. 1299-1302.

J. Cottalorda et al., "Traitement orthopedique de la scoliose: nouvelie technique de prise d'empreinte par procede optique," 1997, Archives de Pediatrie, vol. 4, issue 5, pp. 464-467.

Phip Treleaven et al., "3D body scanning and healthcare applications," 2007, Computer, Jul. 2007, pp. 28-34.

* cited by examiner

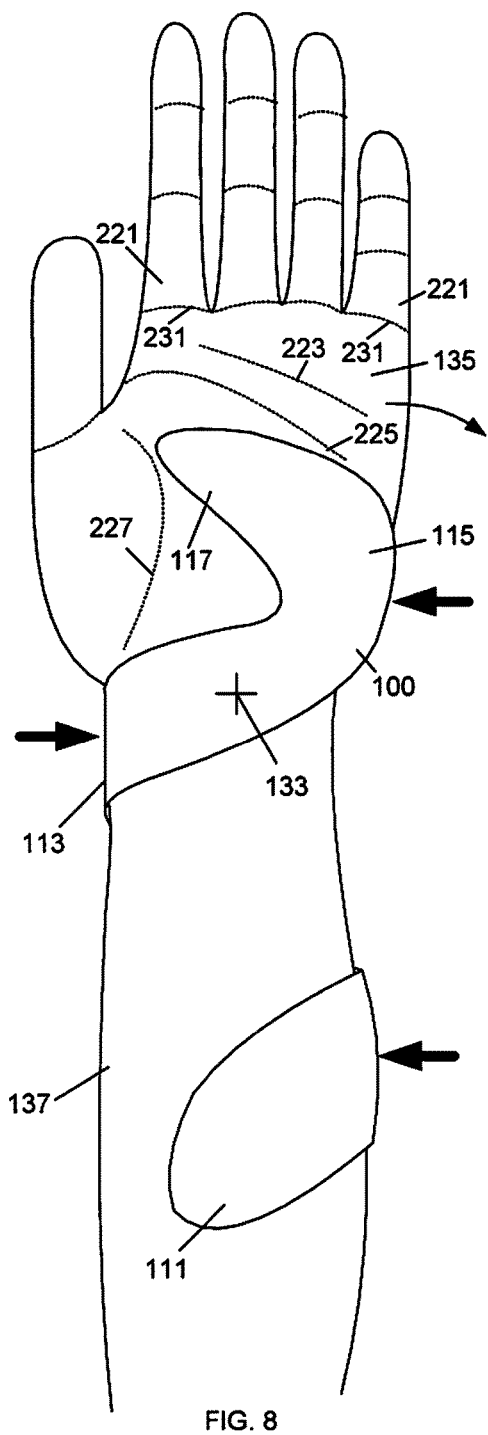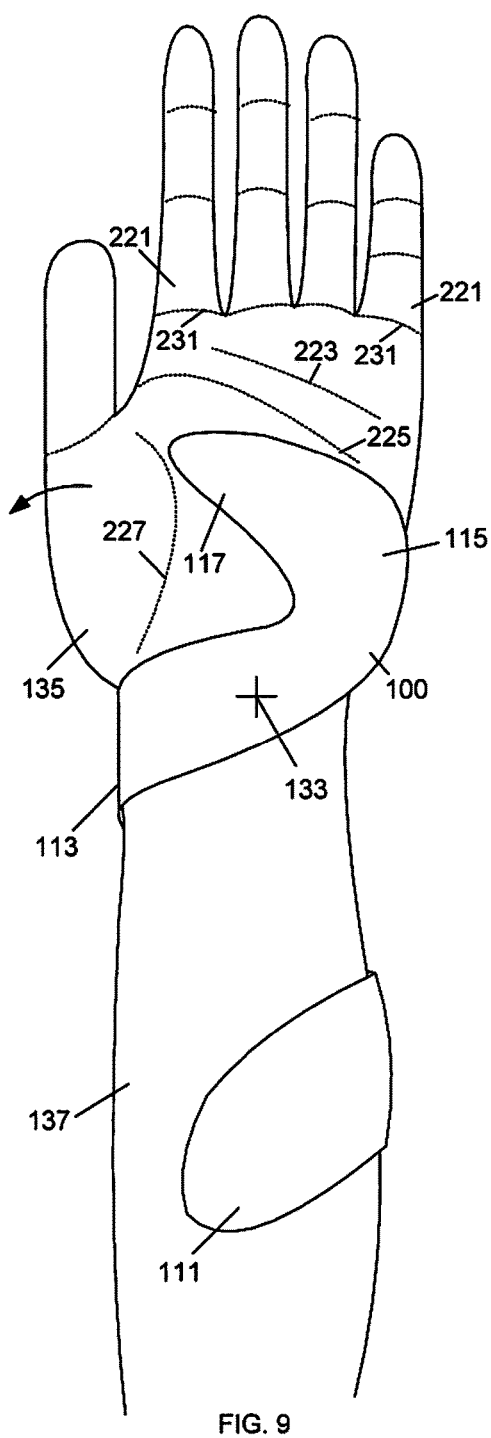

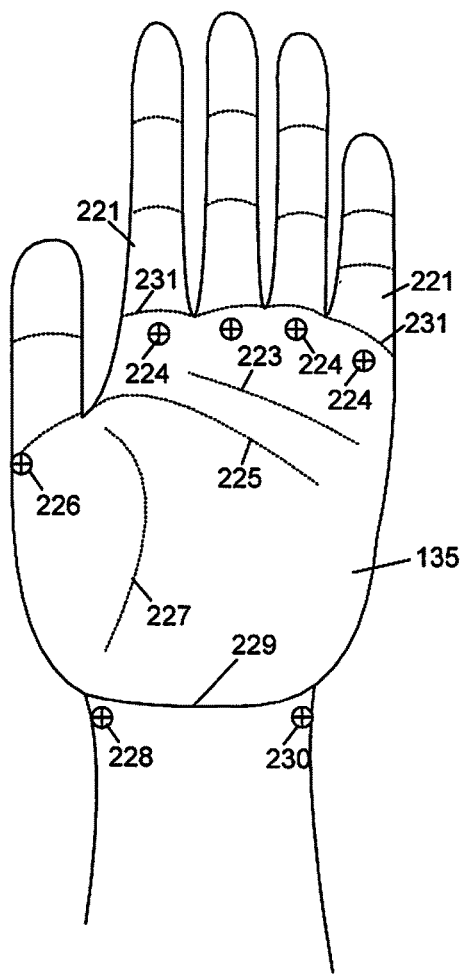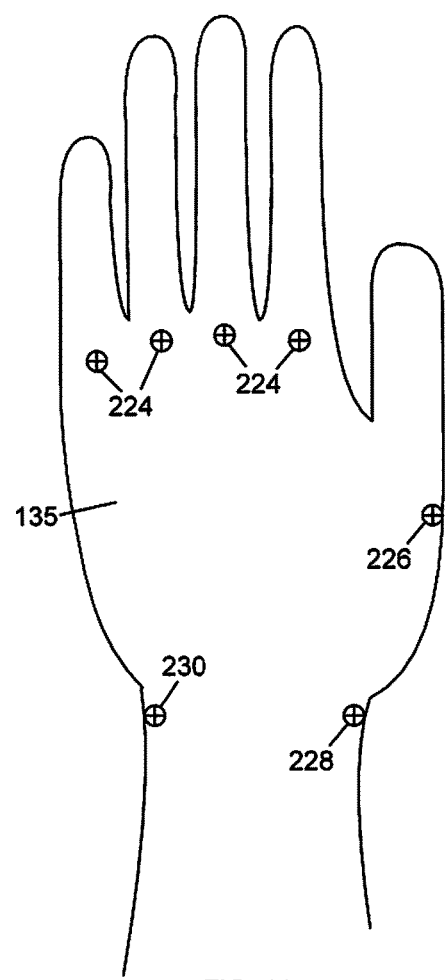
FIG. 10
FIG. 11

SPIRAL BRACE

CROSS REFERENCE TO RELATED APPLICATIONS

This application is a continuation-in-part of U.S. patent application Ser. No. 13/791,678 filed Mar. 8, 2013, which claims priority to U.S. Provisional Patent Application No. 61/720,861, "Spiral Brace" filed Oct. 31, 2012 and is a continuation-in-part of PCT Patent Application No. PCT/US2012/051612, "Adjustable Brace" filed Aug. 20, 2012 which is a continuation-in-part of U.S. patent application Ser. No. 13/214,096, "Adjustable Brace" filed Aug. 19, 2011, this application is also a continuation-in-part of U.S. patent application Ser. No. 14/255,801, "Adjustable Brace" filed Apr. 17, 2014 which is a continuation-in-part of U.S. patent application Ser. No. 13/214,096, "Adjustable Brace" filed Aug. 19, 2011, which is a continuation-in-part of U.S. patent application Ser. No. 12/820,968, "Modular Custom Braces, Casts And Devices And Methods For Designing And Fabricating" filed Jun. 22, 2010 which is a continuation-in-part of U.S. patent application Ser. No. 12/615,196, now U.S. Pat. No. 8,005,651, "Custom Braces, Casts and Devices And Methods For Designing And Fabricating" filed Nov. 9, 2009 which claims priority to U.S. Provisional Patent Application No. 61/112,751, "Brace And Cast" filed on Nov. 9, 2008, U.S. Provisional Patent Application No. 61/168,183, "Orthopedic Braces" filed in Apr. 9, 2009, and U.S. Provisional Patent Application No. 61/185,781, "Bespoke Fracture Brace" filed in Jun. 10, 2009. The contents of PCT Application No. PCT/US2012/051612 and U.S. Patent Application Nos.: 61/720,861, 61/375,699, 61/112,751, 61/168,183, 61/185,781 Ser. Nos. 13/214,096, 12/820,968, 12/615,196, 13/791,678 and 14/255,801 are hereby incorporated by reference in their entireties.

BACKGROUND

A problem with braces is that they can be complicated to secure to the patient's body, uncomfortable to wear and unattractive to look at. Many braces have thick padding that is secured around the injured limb and a rigid structure that prevents the brace from moving which immobilizes the limb. Because of these issues, many patients tend to not wear braces that have been fitted to the patients by their physicians. What is needed is an improved and simplified brace that is easily placed on the patient's body, thin, lightweight, comfortable to wear and more attractive than existing braces.

SUMMARY OF THE INVENTION

The present invention is directed towards a brace that can have a single piece spiral configuration that is placed around an injured limb to support and prevent or restrict movement of the limb. Rather than completely surrounding the injured limb, the spiral brace can wrap one or more full turns in a helical manner around the injured limb. The helical configuration can define a center axis of the brace. The brace body may also have fenestrations to allow air to circulate around the portions of the limb covered by the brace.

The spiral brace can be a single strip of material such as plastic that can be elastically deformed to place the brace on the limb or remove the brace from the limb. However, the brace can also be sufficiently rigid to provide any required support and immobilization of the limb. The brace can be placed on the limb by inserting a portion of the limb in an open portion of the brace so that the center axis of the brace intersects a portion of the limb. The spiral brace can be made of an elastic material and the distal and proximal portion of the brace can be elastically deformed so that the entire brace can be repositioned to wrap around the limb. Once the brace is properly positioned on the limb, the brace can allow axial rotation of the limb, but may also be rigid and strong enough to prevent bending movements of the limb. For example, if the brace is an arm brace, it may allow rotation about a center axis of the brace relative to the forearm and prevent bending of the wrist such as palmar flexion movement of the wrist and hand.

There are various features that make the brace comfortable to wear. The brace can be made of a strong plastic material having a smooth inner surface that can correspond to a digital representation of the injured limb so that the brace will provide a close, custom and personal fit for the patient's limb. Because the brace is thin it can be easily worn under clothing. The brace is also light weight and fenestrated to allow the limb to be exposed to ambient air so that perspiration from the limb can evaporate rather than being trapped by the brace. A spiral arm brace can have thickness that is between about 0.05 inch and 0.50 inch. The pitch of the spiral brace can be greater than 2 inches and less than 6 inches. The proximal portion of the brace can have a width between about 0.5 inch and 2 inches. Because the brace is thin and light weight and may look more like an ornamental object than a medical device, the patient is more likely to wear the inventive spiral brace. The brace can also include ornamental fenestration and topographical designs formed in the outer surface.

In an embodiment, the spiral brace can be used as an arm brace. The brace can have a proximal portion that fits around a forearm portion of the limb and a distal portion of the brace body fits around a hand portion of the limb. The distal hand portion of the brace can have a lower or palmar section that supports a palm of the hand portion and an upper or dorsal section that fits over a dorsum of the hand portion. This configuration can keep the spiral brace in proper alignment with the arm. Because the surface of the palm of the hand is normally concave, the inner surface of the brace body at the lower palmar section of the distal portion includes a convex surface that corresponds to the concave surface of the palm or other convex surfaces of the limb. The brace can also be configured to provide specific types of support for the hand. For example, in an embodiment, the distal limb support at the distal end of the brace may only partially surround the hand and a distal edge of the brace can be adjacent to a palmar digital crease of the hand. The distal edge of the brace may also not extend over proximal phalanx segments of the fingers so that the movement of fingers is not restricted. In an embodiment, the distal limb support of the brace does not extend over a thenar portion of the hand allowing a thumb of the hand to move freely.

If the brace is being used to prevent movement of the wrist to prevent carpal tunnel injury, the spiral brace can be wrapped in a specific manner around the arm. For example, the spiral brace can include a distal limb support that is adjacent to a palmar surface of the hand, a middle section that is adjacent to a posterior surface of the wrist and a proximal limb support at the proximal end of the brace, the proximal limb support is adjacent to an anterior surface of the forearm. If the patient attempts to move the palm in a downward motion, the downward force will cause the middle section to be pressed into the posterior surface of the wrist and the proximal limb support will be pressed into the anterior surface of the forearm. Although the brace can allow some movement, the brace functions to resist this movement to prevent injuries such as median nerve entrapment or carpal tunnel syndrome.

In order to design a custom spiral brace, the injured limb may first be photographed. One or more colored stickers can be applied to the patient's limb and a plurality of markings or points of visible or IR light can be projected to the patient's limb. The light sources can project a pattern of light spots onto the limb. The limb can be placed on a positioning stand between a plurality of infrared (IR) and/or visible light cameras. A doctor may mark the injured areas of the limb with a pen, stickers or any other suitable markers or markings that provide a suitable contrast to the skin of the patient. Some of the markers or markings can be used for position detection or anatomical features such as joints, knuckles, specific areas of bones, etc. Markers or markings can also indicate the areas where the patient is injured such as bone breakage, or swollen areas, etc. Other markers or markings can indicate a desired edge or a seam of the brace. These markers or markings can be captured by the digital photographic images and the marking locations can be used to design the adjustable brace.

From the photographs, a three dimensional digital representation of the limb can be created by photogrammetry, image correlation, depth mapping or any other suitable IR and/or visible light photography based surface topography detection method. From the three dimensional representation of the limb surface topography, a spiral brace can be designed having an inner surface that corresponds to the three dimensional digital representation of the patient's limb. The measurements of the markers or markings from the photographs can be more accurate than measurements of other surface points on the patient. Because the markers can provide more accurate position measurements, the markers can be used for important design data points for the digital representation of the limb and the design of the spiral brace.

In an embodiment, the brace or cast has a smooth inner surface that conforms to the digital representation of the scanned surface of the limb and closely matches the surface measurements of the patient's body. Because the inner surface of the brace accurately conforms to the patient to provide a very close fit, the surface of the limb matches the inner surface of the brace and the brace can be worn by the patient without any padding. The brace can be made of a hard plastic material that provides structural strength to support the limb. In order to be comfortable, the inner surface of the hard plastic brace should also be very smooth. In an embodiment, the inner surface can have a surface finish of less than 500 $R_a$ μ inch. In an embodiment, the innermost surface of the structural layer of the brace can be made of a homogeneous plastic material. In other embodiments, the entire brace can be made of a homogeneous plastic material. A brace or cast that can be worn by a patient without inner surface padding has several benefits including: simplified brace design and construction, less material for fabrication, lower weight, lower profile thickness, better ventilation, no absorption of water, easier cleaning, etc. The inner surface padding in a traditional brace can be a soft cloth that can included a compressible padded material. This inner surface padding can be completely omitted from the inventive brace.

The inventive custom design process is unique because it provides a virtual fitting of the brace to the patient prior to fabrication of the actual device. Because the innermost surfaces of the brace can be designed to be a very close fit to the patient, no additional padding may be needed. No other known system provides the ability to design custom adjustable braces in a virtual manner. In particular, the inventive process can detect markers and/or markings placed on a body and utilize this information to design the adjustable brace based upon the location of the marks.

BRIEF DESCRIPTION OF THE DRAWINGS

FIGS. 8-9 illustrate views of a spiral brace on a hand;
FIGS. 10-11 illustrate dorsal and palmar views of a hand.

DETAILED DESCRIPTION

The present invention is a custom designed spiral brace. The term "spiral" is used to describe the three dimensional curve of a brace that wraps at least one full circumferential turn around an axis of the limb in a generally helical shape. The spiral brace can also have interior surfaces that correspond closely to a digital representation of a portion of a patient's body which can be from an optical scan or photograph(s) of the patient. When a patient injures a limb, the spiral brace can be designed to closely fit around the limb. In order to provide a close fit around the limb, the interior surfaces can be slightly larger than the digital representation of the portion of the patient's body. Thus, the interior surfaces are not an exact match but correspond to the digital representation of the patient's body. The inventive spiral brace can be designed to resist specific types of movement. For example, a spiral brace can be an arm brace that allows movement of the fingers and thumb as well as axial rotation of the hand so that the patient can grasp items, type on a keyboard and rotate door knobs to open doors. However, the spiral brace can prevent bending of the wrist. This can be helpful in the treatment of conditions such as carpal tunnel syndrome.

The different possible movements of the hand and forearm include: flexion, extension, radial deviation, ulnar deviation, pronation and supination. Flexion is the rotation of the hand about the wrist in a downward movement with the arm in a horizontal position. Extension is the rotation of the hand about the wrist in an upward movement. Radial deviation is the movement of the hand about the wrist towards in the direction of the thumb. Ulnar deviation is the rotation of the hand about the wrist towards the small finger. Pronation is the rotation of the forearm that moves the palm from an antior facing position to a posterior facing position which is palm facing down. Supination is rotation of the forearm so that the palm faces anteriouly or palm facing up. The supination rotation is opposite of pronation.

Figure 1:
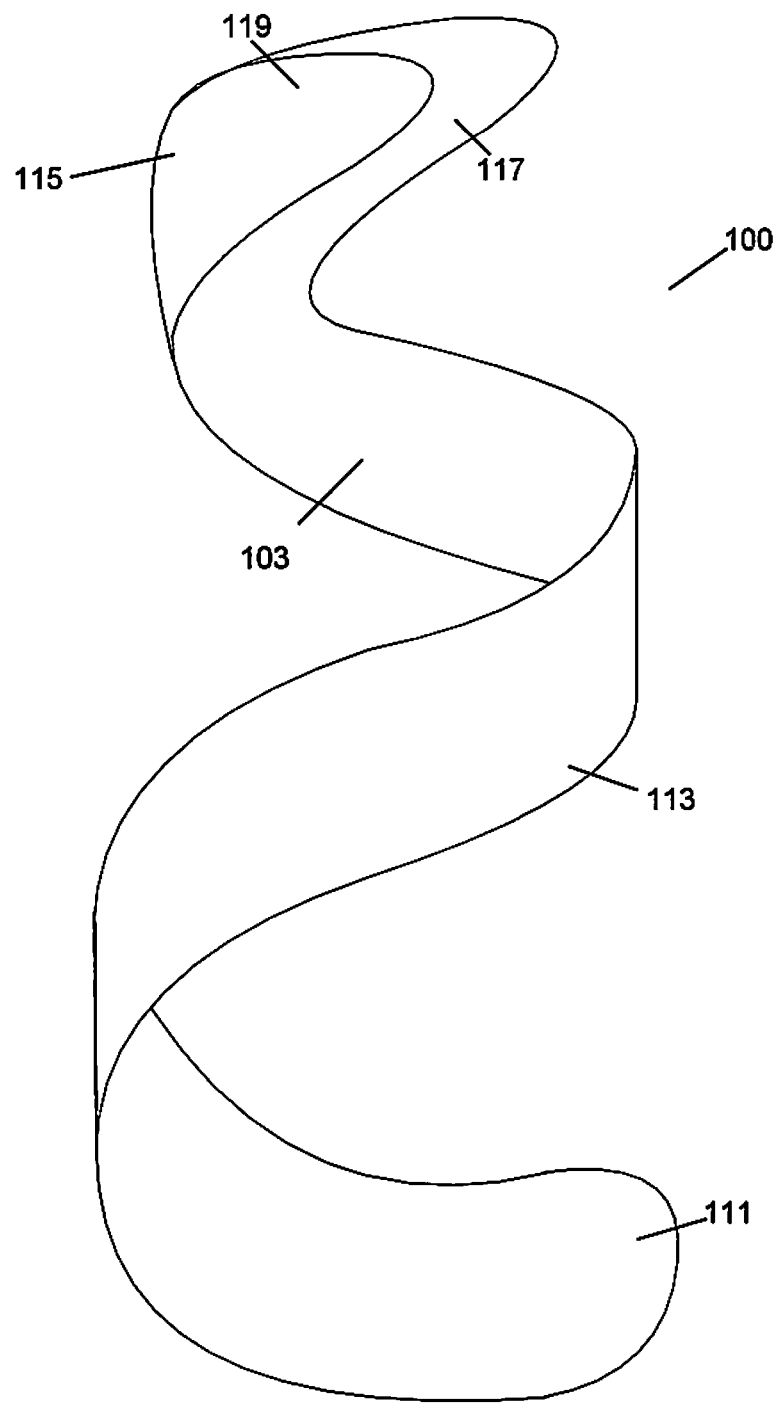
FIGS. 1-3 illustrate an embodiment of a spiral brace.
Figure 2:
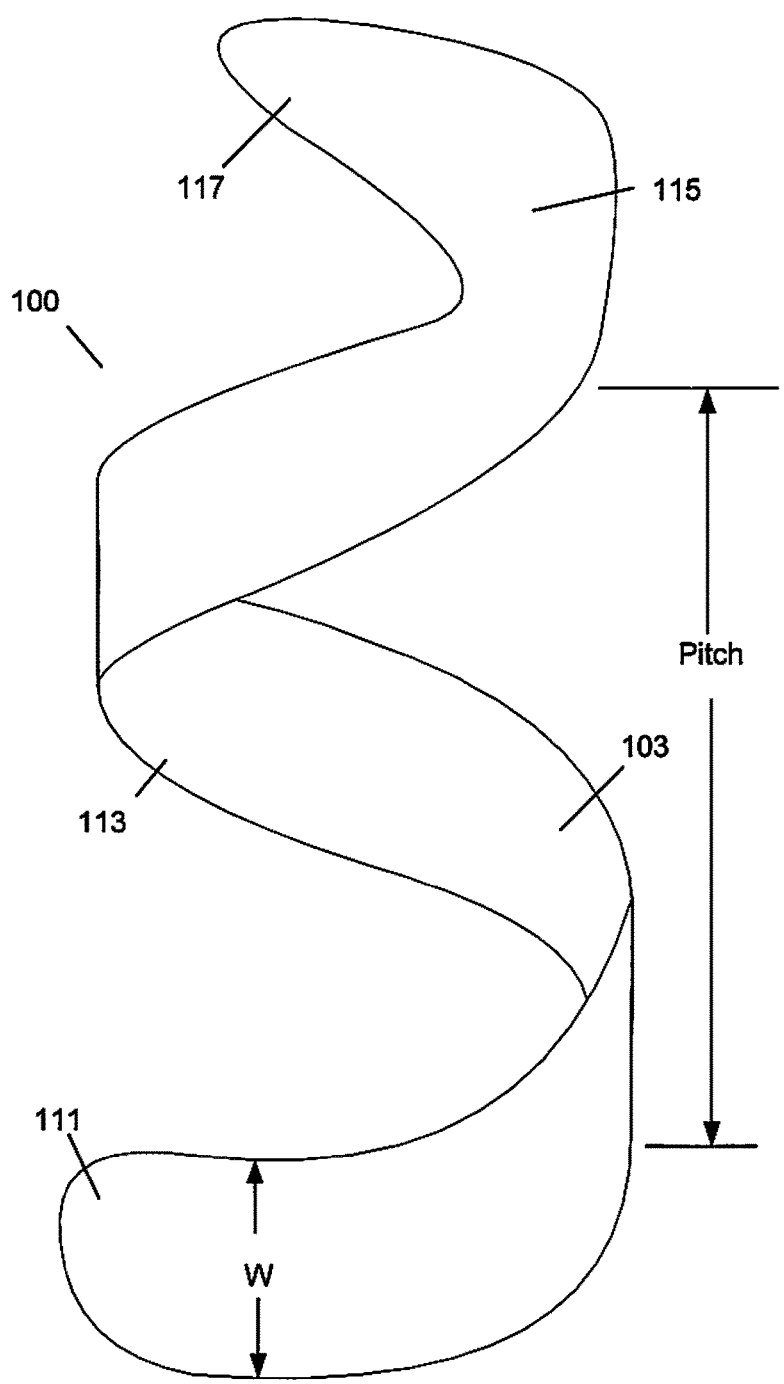

FIG. 1 illustrates a top view and FIG. 2 illustrates a bottom view of an embodiment of a spiral arm brace 100. The spiral arm brace 100 can include a proximal portion 111 that fits around a forearm, a middle portion 113 that fits around a wrist and a distal portion 115 that fits around a hand. The distal portion 115 can have a lower palmar section 117 that supports a palm of the hand portion and an upper dorsal section 119 that fits over a dorsum of the hand. The inner surface 103 of the brace corresponds to a digital representation of the arm. Because the surface of the palm of the hand is normally concave, the inner surface 103 of the brace 100 at the lower palmar section 117 of the distal portion 115 can include a convex surface that corresponds to the concave surface of the palm. Because the surface of the dorsum of the hand is normally convex, the inner surface 103 of the brace 100 at the upper dorsal section 119 of the distal portion 115 can include a concave surface that corresponds to the convex surface of the dorsum.

Figure 3:
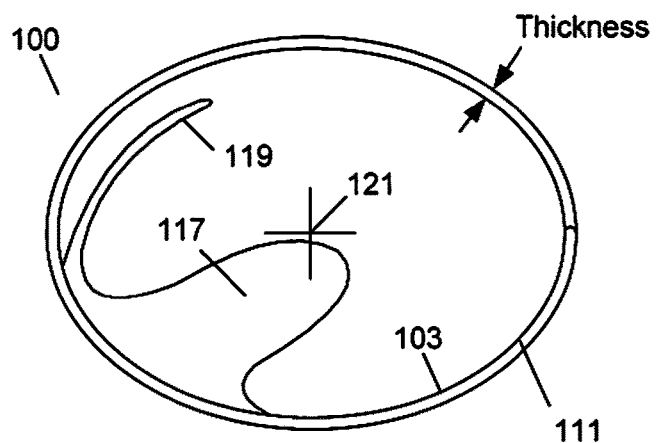

FIG. 3 illustrates an end view of the brace 100 from the proximal portion 111. The spiral brace 100 can define a center axis 121. When the spiral brace 100 is worn on an arm, the spiral brace can allow the hand to rotate about the center axis 121 in pronation and supination. The upper dorsal section 119 and the lower palmar section 117 can fit closely around and against the hand. Thus, the distal portion 115 can remain stationary on the hand. However, the middle portion 113 and the proximal portion 111 can rotate around the forearm of the patient if the wrist is rotated axially about the center axis 121.

There are various features that make the inventive brace comfortable to wear. The inner surface 103 of the brace 100 can correspond to a digital representation of the injured limb so that the brace 100 will provide a custom and personal fit for the patient's limb. Because the brace 100 can be a thin single piece structure, it can be easily worn under clothing. The brace 100 is also light weight and can weigh significantly less than a prior art brace or cast. The brace 100 can be fenestrated to allow the limb to be exposed to ambient air. This ventilation can allow perspiration from the limb to evaporate rather than being trapped between the limb and the brace 100. In an embodiment, the spiral arm brace 100 can have thickness that is between about 0.05 inch and 0.50 inch. In an embodiment, the pitch or the spacing along the axis between the wraps of the body of the spiral brace 100 can be greater than about 2 inches and less than about 6 inches. The proximal portion of the brace can have a width of the body between about 0.5 inch and 2 inches. Because the spiral brace 100 is thin and light weight and may look more like an ornamental object than a medical device, the patient will be more likely to wear the inventive spiral brace 100. For clearer figures, the fenestrations have not been illustrated in the brace illustrations. However, in embodiments, the fenestrations can be a pattern or small or larger holes of any cross-sectional shape that extend through the thickness of the brace 100 and allow air to circulate to the portions of the limb covered by the brace 100. Examples of brace fenestrations are shown in U.S. patent application Ser. No. 12/823,512 which is incorporated by reference in its entirety.

Figure 4:
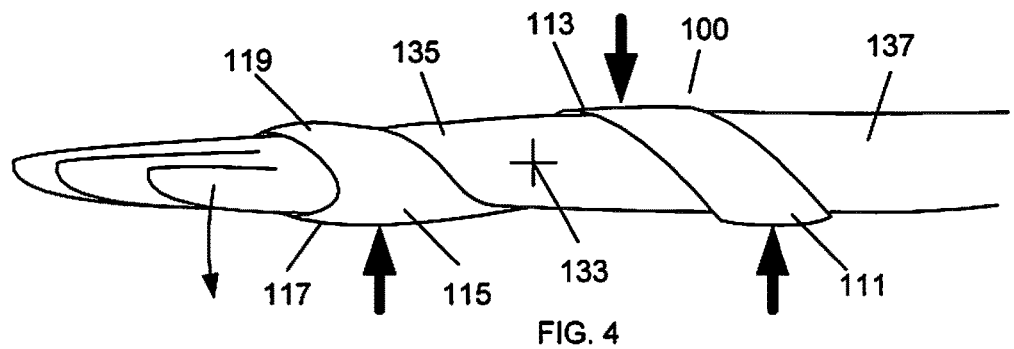
FIGS. 4-7 illustrate side views of an embodiment of a spiral brace on an arm.
Figure 5:
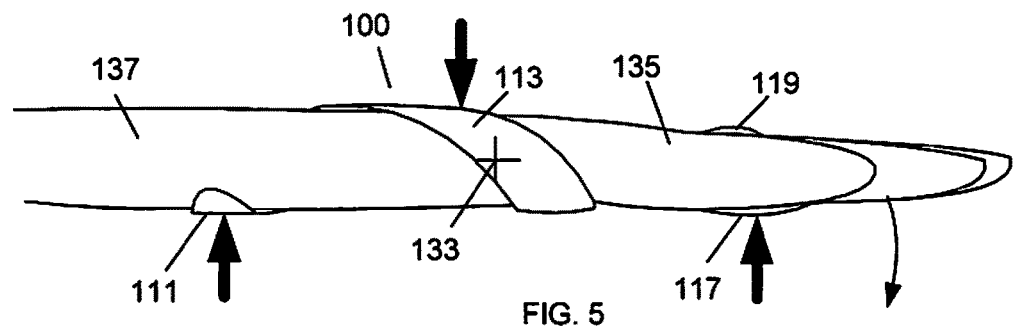

FIGS. 4 and 5 illustrate side views of an arm 137 in an embodiment of the spiral brace 100. As discussed, the distal portion 115 fits around the hand 135, the middle portion 113 is positioned around the wrist 133 and the proximal portion 111 fits around the forearm 131. If the patient attempts to rotate the hand 135 about the wrist 133 in palmar flexion, the brace 100 will resist this motion. More specifically, attempts to rotate the hand down in palmar flexion will cause the palm of the hand 135 to press against the lower (palmar) section 117 of the distal portion 113 which will cause the middle section 115 to press down against the wrist 133. These forces will also rotate the brace 100 so that the proximal portion 111 presses up on the lower surface of the forearm 131.

Figure 6:
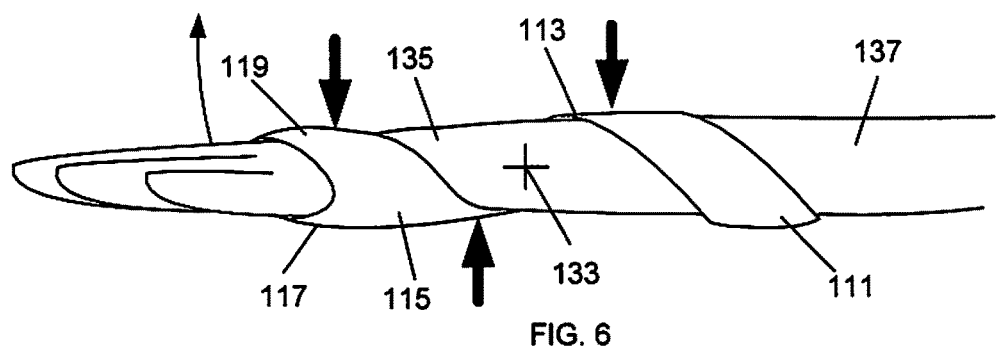
Figure 7:
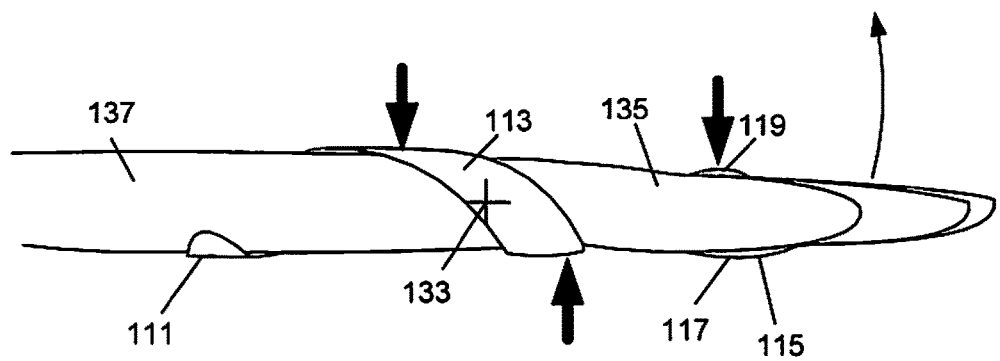

With reference to FIGS. 6 and 7, additional side views of the arm 137 are illustrated. In this embodiment, the patient attempts to move the hand about the wrist 133 in palmar extension. The brace 100 may also resist this motion. The hand 135 can press against the upper dorsal section 119 which can cause the middle section 115 to press up against the wrist 133 and the distal portion 113 to press down on the forearm 137.

With reference to FIG. 8, a palmar side view of an embodiment of the brace 100 on a hand 135 is illustrated. FIG. 9 illustrates a palmar side view of an embodiment of the brace 100 on the hand 135. The movement of the hand 135 in radial deviation is resisted by the brace 100. The distal portion 115 can press against the hand 135 which can cause the middle section 113 can press against the wrist 133 and the proximal portion 111 to press against the forearm 137. In contrast, the illustrated brace 100 may not resist movement of the hand 135 in ulnar deviation. The distal portion 115 may not surround the thumb side of the hand 135. Thus, the hand 135 may be free to rotate in ulnar deviation. In other embodiments, the brace may surround the hand 135 and prevent or restrict rotation in ulnar deviation.

The rigidity of the brace 100 will determine the amount of bending and the type of arm movement that is possible. If the brace 100 has a very rigid construction, the brace 100 may rotate around the arm 137 about the center axis, but the brace 100 may not allow the hand 135 to bend about the wrist. However, if the brace 100 has an elastic construction, some bending of the arm 137 about the wrist may be possible. By knowing the mechanical properties of the material being used and the brace design dimensions and shape, the bending characteristics can be designed into the brace. Thus, the brace 100 can be fabricated so that the axial rigidity is within a specific range based upon the needs of the patient. For example, a brace made for an adult may need to be more rigid than a brace made for a small child in order to provide the required limb movement resistance. The bending characteristics can be quantified in terms of torque per degree of bending or any other suitable units of measurement. For example, a brace 100 can have a rigidity of 10 lbs-inches per degree of bending at the wrist. Thus, it may require about 40 pound-inches of torque to bend the brace 4 degrees. By knowing the physical properties of the brace material, the brace 100 can be designed to have the desired physical characteristics. Although FIGS. 4-8 illustrate the physical resistance of the brace 100 to movement of the wrist in palmar flexion, plarmar extension and ulnar deviation, in other embodiments, the brace can be designed to resist or restrict any other type of limb movement. One of the benefits of the inventive brace is that it can be designed to allow movement of the joints that do not need to be restricted.

With reference to FIGS. 10 and 11, a hand and specific anatomical structures are illustrated. FIG. 10 illustrates a palmar side of the hand and FIG. 11 illustrates a dorsal side of the hand 135. The anatomical structures include: the proximal phalanx segments 221 of the fingers, the palmar digital creases 231, the distal palmar crease 223, the proximal palmar crease 225, the thenar crease 227 and the wrist crease 229. Because the fingers bend towards the palmar side of the hand 135, these creases may only be visible on the palmar side of the hand 135. The hand 135 may also include anatomical points that can be marked with stickers or any other type of markings that can improve the accuracy of the measurements for these points. These marked anatomical points can include: finger knuckles 224, the thumb knuckle 226, radial styloid 228, and the ulnar styloid 230. The knuckle and styloid points may be marked on either side of the hand. In an embodiment, the knuckle and styloid points can be marked on one side of the hand 135 and the system can identify these points and points for these anatomical features on the the opposite side of the hand. For example, if the knuckle and styloid points are identified on the surface of the dorsal side, the system can process this information and also identify the locations of the knuckle and styloid points on the surface of the opposite palmar side of the hand 135. The system can also function in the reverse manner with the system identifying points marked on the dorsal side of the hand based upon markings on the palmar side of the hand In an embodiment, the system can use the location information to design a portion or the entire the brace. The system can design the brace either with additional input from a brace designer or fully automatically.

By identifying and referencing these visible anatomical features of the hand during the design process, the spiral brace can be designed to cover specific areas of the hand to prevent specific types of movement or avoid certain areas of the hand to allow movement of specific joints or parts of the hand or limb. In an embodiment, the photographic process used to create a digital representation of the body may be able to identify these features and provide graphical identifications of these features on a display coupled to a design computer. The brace can then be designed to restrict or accommodate movement of specific areas of the hand.

With reference to FIGS. 8-9 and 12-15, a spiral brace 100 shown is shown on an arm. The lower palmar section 117 of the distal portion 115 of the brace 100 can have an inner surface that corresponds to the palm portion of the hand. This lower palmar section 117 may not cover the distal palmar crease 223, the proximal palmar crease 225 or the proximal phalanx segments 221. Therefore the movement of the fingers is not restricted by the spiral brace 100. Similarly, since the lower palmar section 117 does not extend over the thumb or the thenar crease 227, the movement of the thumb is also not restricted. In this embodiment, the brace 100 covers the wrist crease and the brace 100 may resist or prevent the rotation of the hand about the wrist as illustrated in FIGS. 4 and 5.

Figures 12, 13:
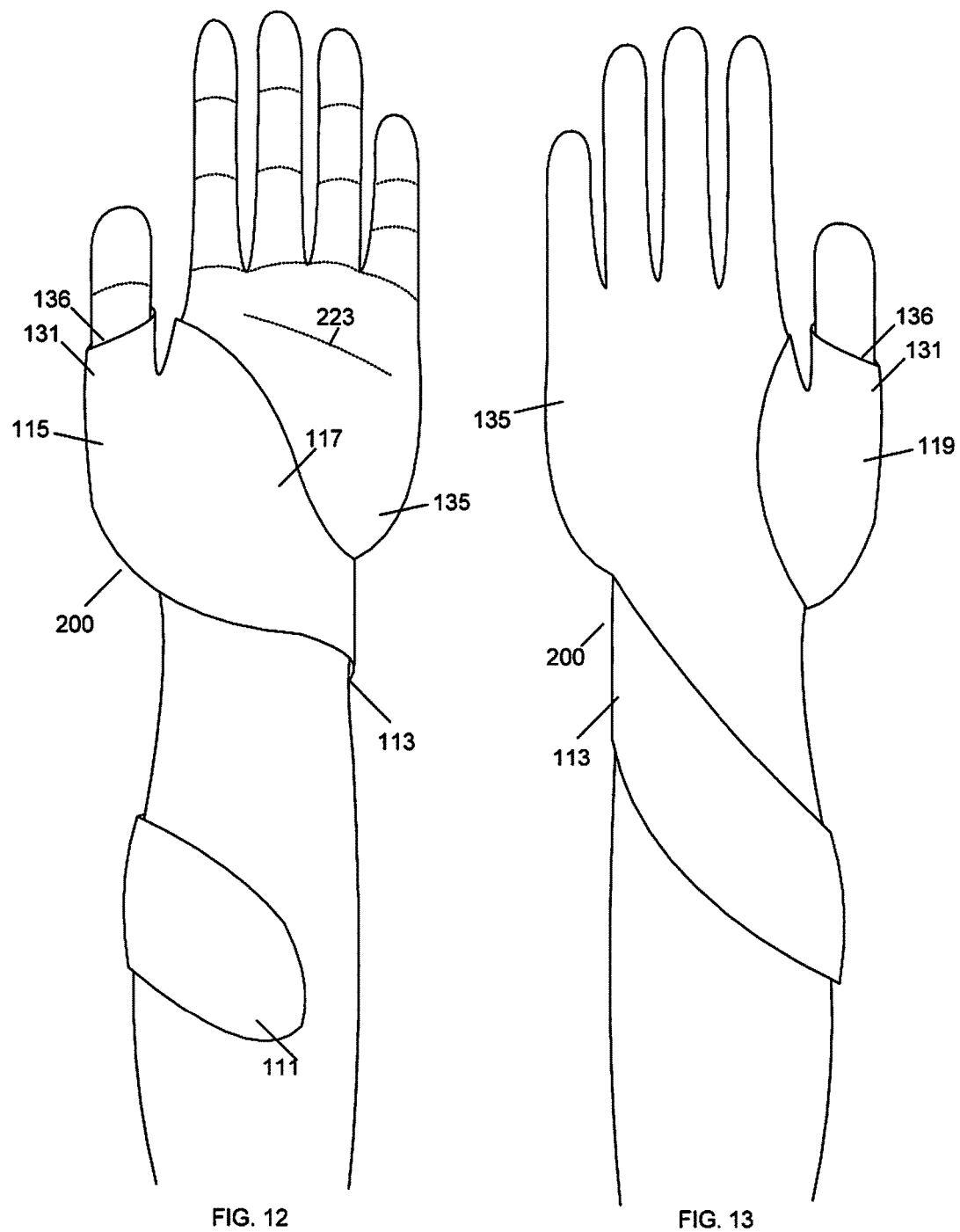
FIGS. 12-13 illustrate views of a spiral brace that restricts thumb movement.

With reference to FIGS. 12 and 13, in an embodiment of the spiral arm brace 200 is illustrated that includes a thumb section 131 that restricts the movement of the thumb, the fingers and the hand. FIG. 12 illustrates a bottom or palmar view of the spiral brace 200, and FIG. 13 illustrates a top or dorsal view of the brace 300. In this embodiment, a distal portion 115 of the spiral brace 300 includes a thumb section 131 that surrounds at least a portion of the thumb. The thumb section 131 extends from both the lower palmar section 117 and the upper dorsal section 119. Since the thumb is surrounded by the thumb section 131, the spiral brace 200 restricts the movement of the thumb relative to the hand. Because the brace 200 can have an inner surface that corresponds to a digital representation of the hand, the thumb section 131 can have a very close fit with the thumb that is comfortable. Because there can be very little space between the thumb and the inner surface of the thumb section 131, the brace 200 can partially or completely restrict the thumb movement. In this embodiment, the distal section 115 may also cover the thenar crease 227 which can further restrict movement of the thumb. In order to place the brace 200 onto the arm, the hand may first be placed into the distal portion 115 with the thumb placed through the thumb hole 135 and the palm against the inner surface of the lower palmar section 117. The middle section 113 and the proximal section 111 can then be elastically moved around the arm and into proper position. Because the thumb is placed through the thumb hole 136 in the brace 200, the brace 200 can resist movement of the hand 135 in palmar flexion, palmar extension, radial deviation and ulnar deviation.

Figures 14, 15:
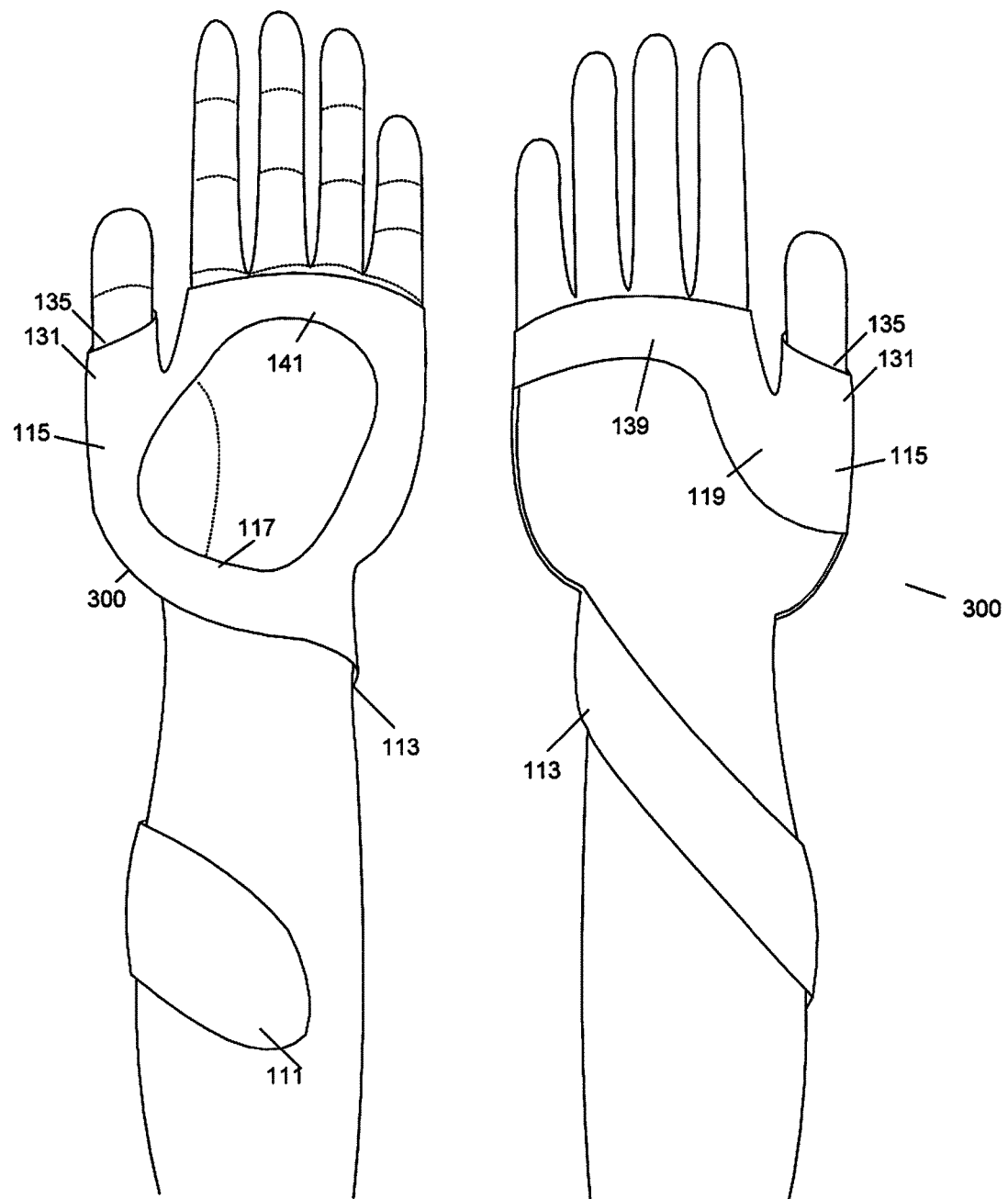
FIGS. 14-15 illustrate views of a spiral brace that restricts thumb and finger movement.

With reference to FIGS. 14 and 15, an embodiment of a spiral arm brace 300 is illustrated that prevents movement of the hand and the lower thumb and can also restrict the movement of the fingers. In this embodiment, the distal portion 115 may extend around the perimeter of the hand and include a thumb section 131 and a thumb hole 135. The lower surface 117 may also include a lower finger section 141 that is adjacent to the proximal phalanx segments of the fingers. The upper dorsal section 119 can include an upper finger section 139 that extends over the knuckles of the hand. Although, the thenar crease 227 may be partially exposed by a hole or holes in the distal portion 115, the hand movement may be restricted by the brace 300 by the distal portion 115. In order to place the brace 300 onto the arm, the hand may first be placed into the distal portion 115 with the thumb placed through the thumb hole 135 and the fingers placed between the lower finger section 141 and the upper finger section 139. The middle section 113 and the proximal section 111 can then be elastically moved around the arm and into proper brace position. In alternative embodiments, the brace 300 can have individual holes for each of the fingers between the upper finger section 139 and the lower finger section 141. Because the thumb is placed through the thumb hole 136 and the fingers are placed between the lower finger section 141 and the upper finger section 139 in the brace 200, the brace 300 can resist movement of the hand 135 in palmar flexion, palmar extension, radial deviation and ulnar deviation.

In an embodiment, the spiral braces disclosed by the application are fabricated using a 3D printing machine, as a single integrated structure. Although, the braces are shown for hands and forearms, in other embodiments, the inventive braces may also be designed and used for any other portion of the patient's body including elbows, feet, legs, ankles, knees, back, neck, shoulders, and other portions of the body.

The brace can have a smooth inner surface that corresponds closely to the patient's body and may also have an integrated construction. The cast or brace can be designed by an industrial designer using a Computer Aided Design (CAD) computer program. The mechanical data for a patient can be obtained from visible or infrared (IR) light photographs of the patient's body or limb. This body topography can be determined from the photographs and the topography data is then digitized and input into a CAD program that is referenced to design the cast or brace. An example of a suitable CAD program is Pro/Engineer by Parametric Technology Corporation. Other CAD software includes: SolidWorks by SolidWorks Corporation a subsidiary of Dassault Systèmes, S. A. For simplicity, the inventive custom brace, cast or device will be described as a leg brace, however the same processes can be used to form an arm or back brace or any other body brace, cast or device. The brace can be a hard and strong structure that is designed to surround and support the injured portion of the body or limb.

For example, a leg brace is created for a patient using a CAD system. The leg brace can include an upper leg, knee, lower leg, and foot and have an interior surface that matches the mechanical dimensions and surface contours of the patient's leg. In order to accurately create an interior surface that matches the patient's leg, the surface counters of the user's leg are measured. The measurement of the outer surface of the leg can be obtained in several different ways. In a preferred embodiment, a photogrammetry, depth mapping or image correlation technique or other type of photographic surface detection method is used to obtain the outer surface measurements which can be a set of 3-dimensional coordinates that define the outer surface of the patient's leg or any other body part.

Photogrammetry in its broadest sense reverses the photographic process by converting flat 2-dimensional images of objects back into the real 3-dimensional object surface. Two or more different photographs can be required to reconstruct a 3-dimensional object. In a perfect photogrammetry process, two photographs would provide enough information to perfectly reconstruct the 3-dimensional object. Unfortunately, the photography and measuring process are generally not perfect so the reconstruction of the 3-dimensional object based upon two photos will also have defects. The photogrammetry object measurement process can be improved by taking more photographs and using the extra information to improve the accuracy. The photogrammetry process will produce a set of 3-dimensional coordinates representing a surface of an object from the measurements obtained from the multiple photographs.

Photogrammetry uses the principle of triangulation, whereby intersecting lines in space are used to compute the location of a point in all three, XYZ dimensions. In an embodiment, multiple cameras are used to photograph the leg or body part simultaneously. In other embodiments, a light from a light source that is a known distance from a camera is projected onto a patient and a photograph of the patient is taken. By triangulating each of the points of light, the distances from the camera to each point of light can be determined. In order to triangulate a set of points one must also know the camera positions and aiming angles also called the "orientation" for all the pictures in the set. A process called resection is used to determine the camera positions and aiming angle calculations for each camera. The cameras should also be calibrated so their errors can be defined and removed.

Triangulation is the principle used by photogrammetry to produce 3-dimensional point measurements. By mathematically intersecting converging lines in space, the precise locations of the points can be determined. Photogrammetry can simultaneously measure multiple points with virtually no limit on the number of simultaneously triangulated points.

By taking pictures from at least two or more different locations and measuring the same target in each picture a "line of sight" is developed from each camera location to the target. Since the camera locations and aiming directions are known, the lines can be mathematically intersected to produce the XYZ coordinates of each targeted point. When a pattern of IR or visible light points are projected onto the patient, triangulation can also be used to determine the locations of these points based upon the distance between the light source and the camera and the detected angles of the points.

Resection is the procedure used to determine the coordinates of the object from photograph data, based upon the camera positions and aiming directions, also known as the orientation of the camera. Typically, all the points that are seen and known in XYZ coordinates in the image are used to determine this orientation. For an accurate resection, you may have at twelve or more well-distributed points in each photograph. If the XYZ coordinates of the points on the object are known, the camera's orientation can be computed. It is important to realize that both the position and aiming direction of the camera are needed for resection. It is not sufficient to know only the camera's position since the camera could be located in the same place but be aimed in any direction. Consequently, the camera's position which is defined by three coordinates, and where it is aimed which is defined by three angular coordinates must be known. Thus, although three values are needed to define the X, Y and Z coordinates of a target point, six values may be required to define a point on a picture, XYZ coordinates for position, and XYZ angles for the aiming direction.

The surface being photographed should also have a minimum number of well-distributed reference points that appear on each photograph and for an accurate surface measurement. The reference points can be visible marks placed on the object that provide a visible contrast that will be clearly shown on the photographs. There should be at least twelve well-distributed reference points on each photograph and at least twenty points for the entire surface of the object. The reference points should be evenly distributed on the object and throughout the photograph. The surface of the object can be more accurately measured with a larger number of reference points.

In an embodiment, the patient's natural features including: freckles, spots, wrinkles, pores and other features can be used as the reference points. Alternatively, IR or visible light can be projected onto the patient to provide a pattern or a random distribution of many projected light points on the patient which are then photographed to provide reference points for surface topography measurements. Any of these types of points can be used alone or in combination. For example, a surface detection method may include projecting a plurality of IR light points onto a patient and place one or more stickers on the patient. Photographs of the patient can detect both the locations and/or positions of the light points and the stickers. The stickers may provide more contrast with the patient and measurements taken from the stickers may result in more accurate location measurements. Thus, the stickers may be used to one or more important locations on the limb. It is also possible to mark the patient's skin with ink markers, stickers, and the like and in an embodiment, the patient or patient's limb can be covered with a form fitting material such as an elastic cotton tube, stockinette, leotard, or body suit.

In an embodiment, a computer program processes the photographic measurements to produce the final XYZ coordinates of all the measured points. In order to do this, the program triangulates the target points and resects the pictures. The program may also calibrate the camera. Typical accuracies of the three dimensional measurements can be very high under ideal operating conditions. For example, the measurements can be accurate to 50-100 microns (0.002" to 0.004"). However, the accuracy of a photogrammetric measurement can vary significantly since accuracy depends on several inter-related factors. Important accuracy factors include: the resolution and quality of the camera, the size of the object being measured, the number of photographs taken, and the geometric layout of the pictures relative to the object and to each other.

Photogrammetric measurements can be dimensionless. To scale a photogrammetric measurement, at least one known distance is required. The known distance can be a distance marked on the object, a known distance between cameras or a known distance between a light source and a camera. For example, if the actual coordinates for some targeted points are known, the distances between these points can be determined and the points can be used to scale the measurement. Another possibility is to use a fixture with targets on it and measure the fixture along with the object. Because the distance between the targets on the fixture is known, it can be used to scale the other measurements between reference points on the object. Such fixtures are commonly called scale bars. The patient topography dimensions can also be determined by knowing a distance between two cameras and the angles of lines between the cameras and the points on the patient. From this information, the distances between the cameras and the points on the patient can be determined by triangulation. Similarly, the patient topography dimensions can also be determined by knowing a distance between a light beam source and a camera, an angle of the light beams from a source and the angles of the light points detected by the camera. From this information, the distances between the camera and the light points on the patient can be determined by triangulation. The light can be infrared and the camera can be an infrared camera that produces infrared photographs. The surface measurement information obtained from the photographs can be used to generate a digital representation of at least a portion of the patient.

In an embodiment, the inventive method is used to make a cast or a brace for an injured limb. A series of photos are taken of the injured limb. If the bone is broken, fracture should be reduced before the photos are taken. The photogrammetric processing methods described above are then used to obtain the surface coordinates of the injured limb. In order to define common surface points on the limb, reference points can be placed on the limb. The reference points can simply be any contrasting color points, patterns, shapes, objects, symbols or other optical indicators which are easily visible. The reference points can be black or colored ink marks that are placed on the body with a pen. In other embodiments, the reference points can be lights such as visible light, infrared light, points or grids, stickers or objects or any other visible point of reference. For example, circular adhesive stickers which have a contrasting color can be placed on the patient and photographed. The stickers can provide accurate reference points which can be used to produce the digital representation of the patient's limb and/or body. In the preferred embodiment, the reference points are placed and evenly distributed around the entire limb or portion of the body that the brace is being constructed for.

Figure 16:
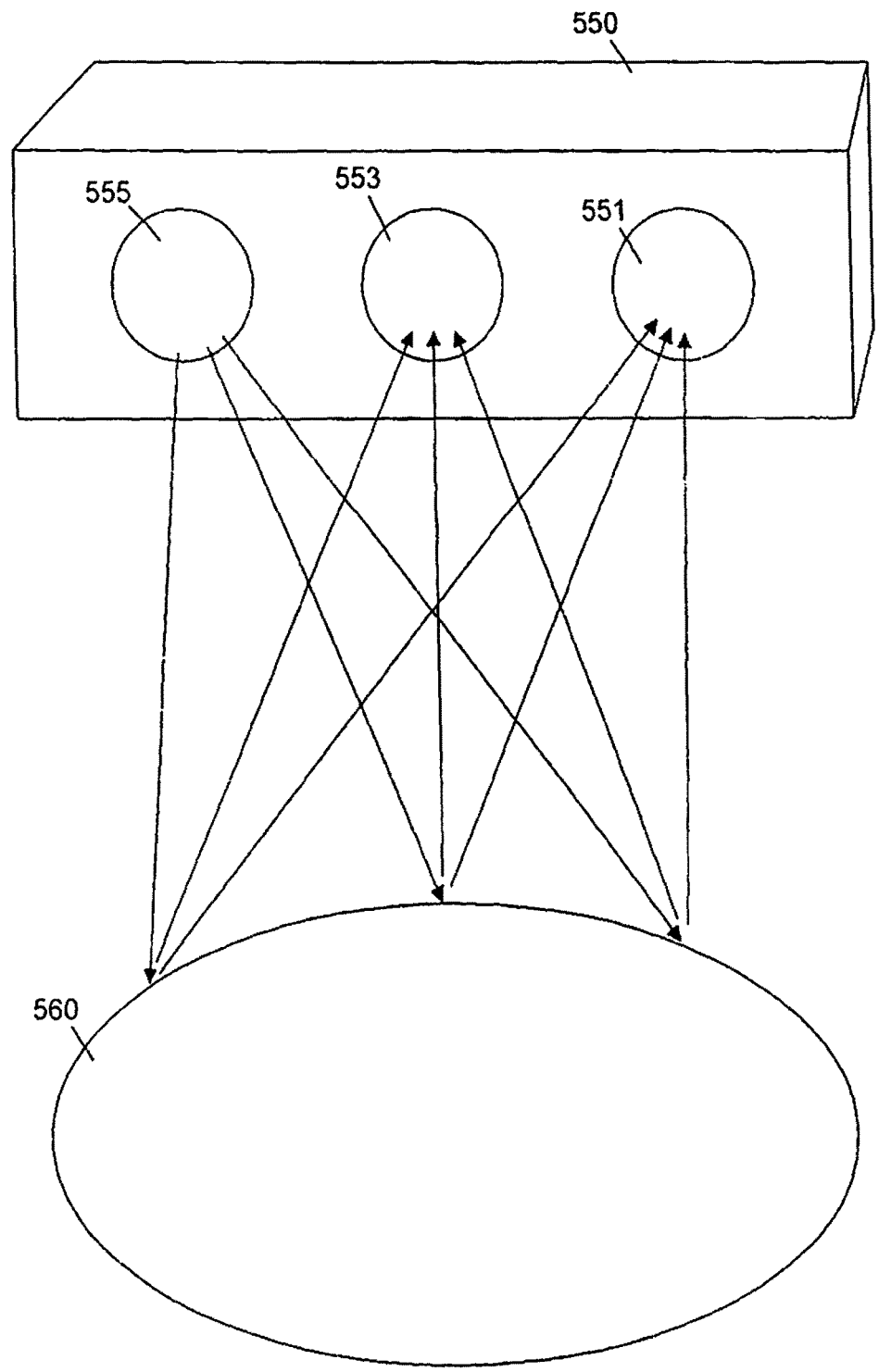
FIGS. 16-19 illustrate IR and visible light photographic systems for detecting a surface of a patient.

With reference to FIG. 16, in an embodiment the three dimensional surface data of a patient can be obtained using an optical device comprising a color image camera 551, an infrared (IR) camera 553 and an infrared (IR) light source 555 coupled to a signal processor. The IR light source 555, IR camera 553 and color image camera 551 can all be mounted on one side of the optical device 550 so that the color camera 551 and IR camera 553 have substantially the same field of view and the IR light source 551 projects light within this same field of view. The IR light source 555, IR camera 553 and color image camera 551 can be mounted at fixed and known distances from each other on the optical device 550. The color image camera 551 can provide color information for the patient's limb 560 or portion of the patient within the viewing region of the camera 551. The IR camera 553 and IR light source 555 can provide distance information for each area of the patient's limb 560 exposed to the IR light source 555 that is within the viewing region of the IR camera 553. The infrared light source 555 can include an infrared laser diode and a diffuser. The laser diode can direct an infrared light beam at the diffuser causing a pseudo random speckle or structured light pattern to be projected onto the patient's limb 560. The diffuser can be a diffraction grating which can be a computer-generated hologram (CGH) with a specific periodic structure. The IR camera 553 sensor can be a CMOS detector with a band-pass filter centered at the IR laser wavelength. In an embodiment, the color image camera 551 can also detect the IR light projected onto the patient's limb 560.

Figure 17:
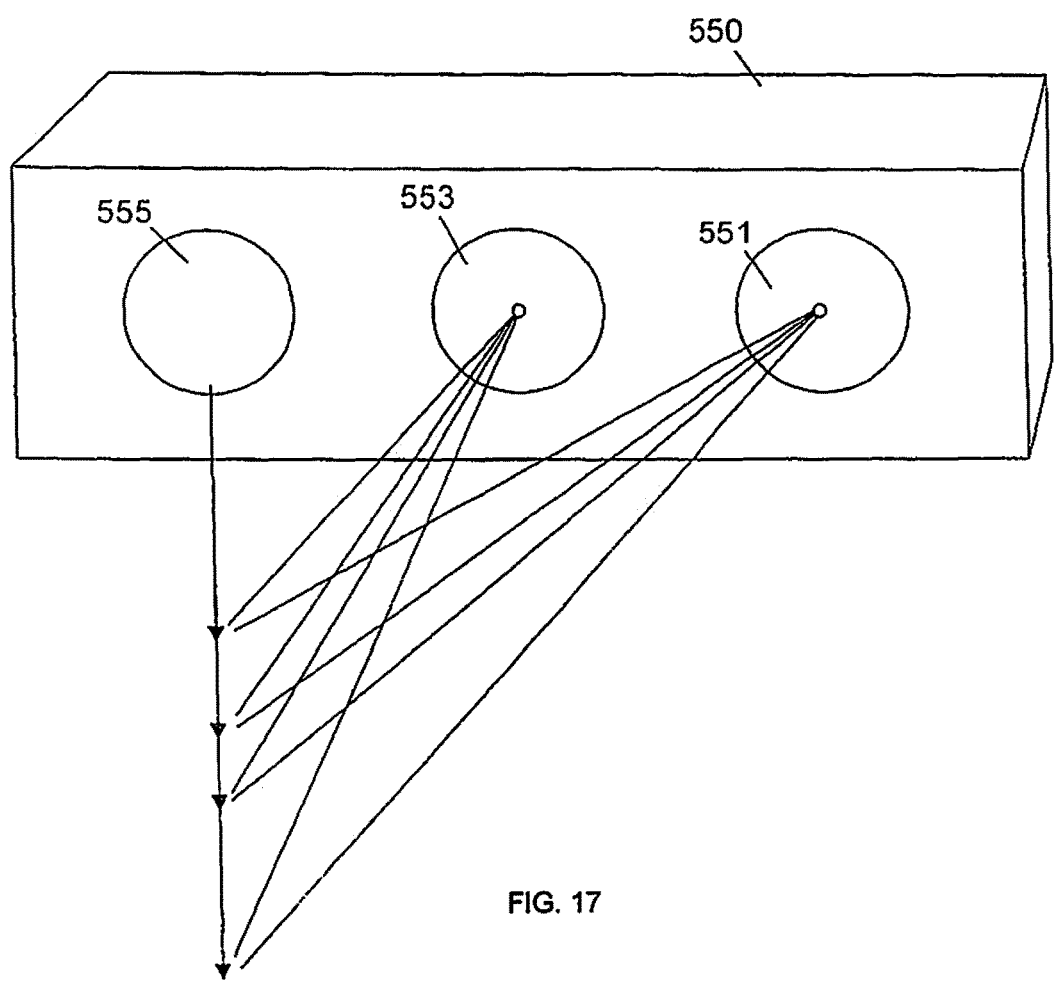

With reference to FIG. 17, the optical device 550 can detect the distance between the infrared camera 553 and the IR light on the patient because the camera 553 sees the patient's limb at a different angle than the infrared light source 555 and the distance between infrared light source 555 and IR camera 553 is defined. The principle of structured light distance sensing is that given a specific angle between IR light source 555 and IR sensor 553 for each point of light on the patient's limb and a distance between the object and the IR light source 555 or IR camera 553 or color camera 551 can be determined by triangulation. The angles of the light points on the patient's limb detected by the IR camera 553 and the color camera 551 will change depending upon the distance of the patient from the optical device 550. In an embodiment, a calibration process can be used to determine the angles of each light point on a plane at different distances from the optical device 550. By knowing the angles and corresponding distances for each point of IR light and distance of the points of light from the optical device 550 can be determined. These distance calculations for an object can also be known as three dimensional mapping. The distance value for each light point can also be matched with the visible color image data so that color and distance information for each pixel of a patient image can be determined and stored.

Because a single picture can capture the patient in a fixed position, the IR light source 555 can project the IR light on the patient and the IR camera 553 can take a single photograph of the patient 560. The color camera 551 may also simultaneously take a single photograph of the patient's limb 560. In other embodiments, multiple IR or color photographic images can be taken of the patient's limb 560 in different positions and the corresponding image shifts are directly related to distance from the camera. Each successive photographic image is served as a reference photograph for the next frame calculation so that the movement of the patient can be detected and the changes in the three dimensional mapping can be recorded.

Figure 18:
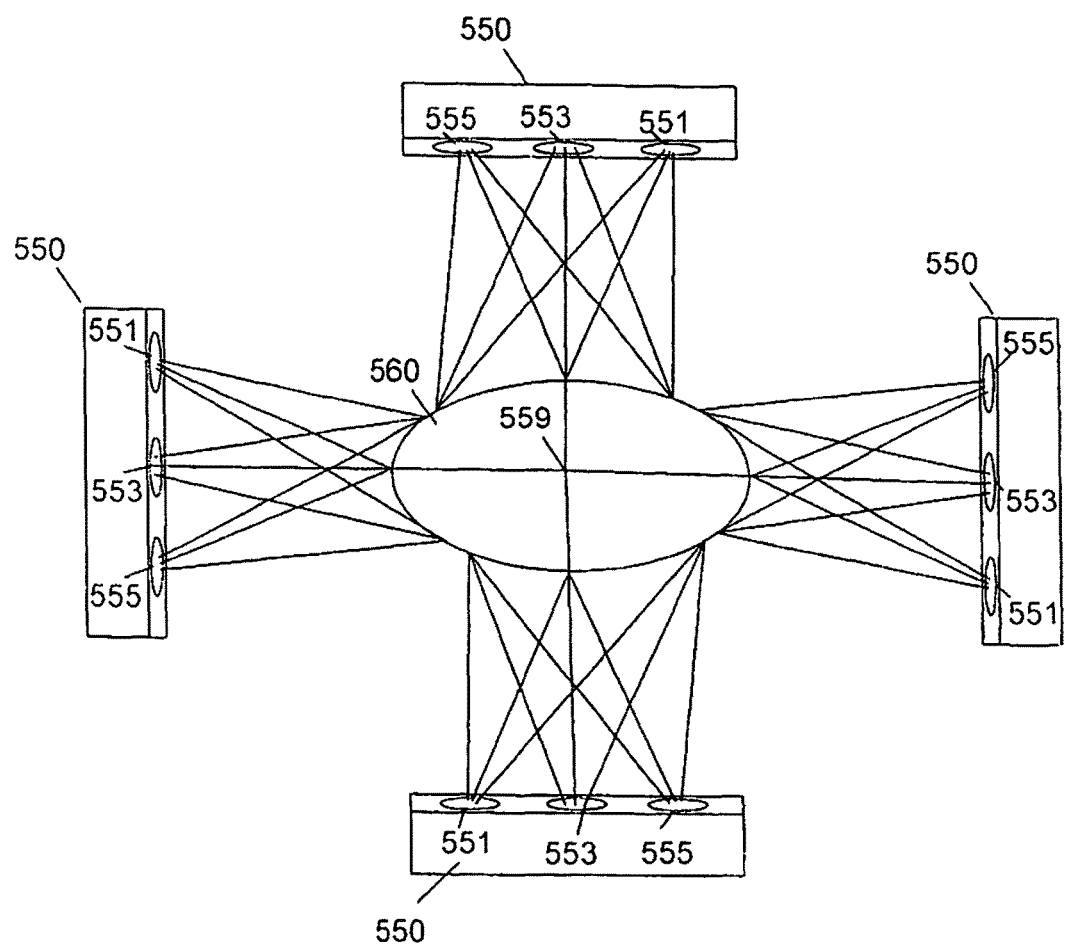

As discussed, the IR camera can detect the light pattern projected onto the patient's limb and through triangulation, the distance between the IR camera and color camera and each point of the light pattern on the patient can be determined. However, the distance information for the points can only determine a three dimensional surface of the patient's limb or a portion of the patient's limb that are detected by the IR camera 553 or the color camera 551. With reference to FIG. 18, in order to determine a three dimensional surface around a patient's limb, multiple optical devices 550 can be placed around the patient and the three dimensional surface information from each of these cameras can be combined to determine the three dimensional surfaces around a circumference of a patient's limb which can be a digital representation of the limb of the patient. In an embodiment the IR light from each of the IR light sources 555 can be emitted simultaneously and the photographs from all of the IR cameras 553 and color cameras 551 can be taken simultaneously. In other embodiments, the IR light sources 555 can interfere with the IR cameras 553 that are not part of the same optical system 550. Rather than projecting IR light from all of the IR light sources 555 at the same time, the optical systems 550 can be configured to sequentially illuminate with IR light and photograph the patient's limb 560. A first optical system 550 will emit the IR light and take IR and color photos of the patient's limb 560. The first optical system 550 can then stop projecting IR light onto the patient's limb 560 and the second optical system 550 can then emit the IR light, take IR and color photos of the patient's limb 560. The second optical system 550 can then stop projecting IR light onto the patient's limb 560. This described process can be sequentially repeated for the remaining optical systems 550.

After taking the IR photographs, surface data for different sides of the patient's limb 560 can be combined from the optical systems 550 in various different ways. For example, the multiple IR cameras 553 can produce distance information for the photographed patient's limb 560 that can be combined using a photogrammetry process to determine a full or partial circumferential three dimensional representation of the patient's limb 560. The surface data from the optical systems 550 will include some of the same surface areas of the patient's limb 560 that were also captured by at least two of the adjacent optical system 550. Because the three dimensional shape data is the same, the system can identify these matching surface shapes and combine the surface data to obtain continuous surface data for the photographed portion of the patient's limb 560. In an embodiment, the optical systems 550 can be aligned around the patient 560 with the IR cameras 553 radially aligned in a planar manner and directed towards a center point 559 within a cross section of the patient's limb 560. The optical systems 550 can each produce surface data for a portion of the patient's limb 560. Because the IR photos are taken on a common plane, the surface data from the different optical systems 550 can be joined by determining the distance of the surface data from the center point 559. In an embodiment, a first set of calibration IR and/or color photographs can be taken by the optical systems 550 of a physical center point marker 559 without the patient's limb 560. IR and/or color photos can then be taken of the patient 560. From this information, the position of the center point 559 relative to the surface data or digital representation of the patient 560 can be determined. By knowing the distances and alignment of the surface data to a common center point 559, the surface data from the different optical systems 550 can be combined. In an embodiment, the optical systems 550 can be arranged on direct opposite sides of the patient's limb 560. Although four optical systems 550 are shown, in other embodiments, two or more optical systems 550 can be used to obtain the surface data for the patient's limb 560. Three optical systems 550 may be required to have some overlapping surface data for the patient's limb 560.

Figure 19:
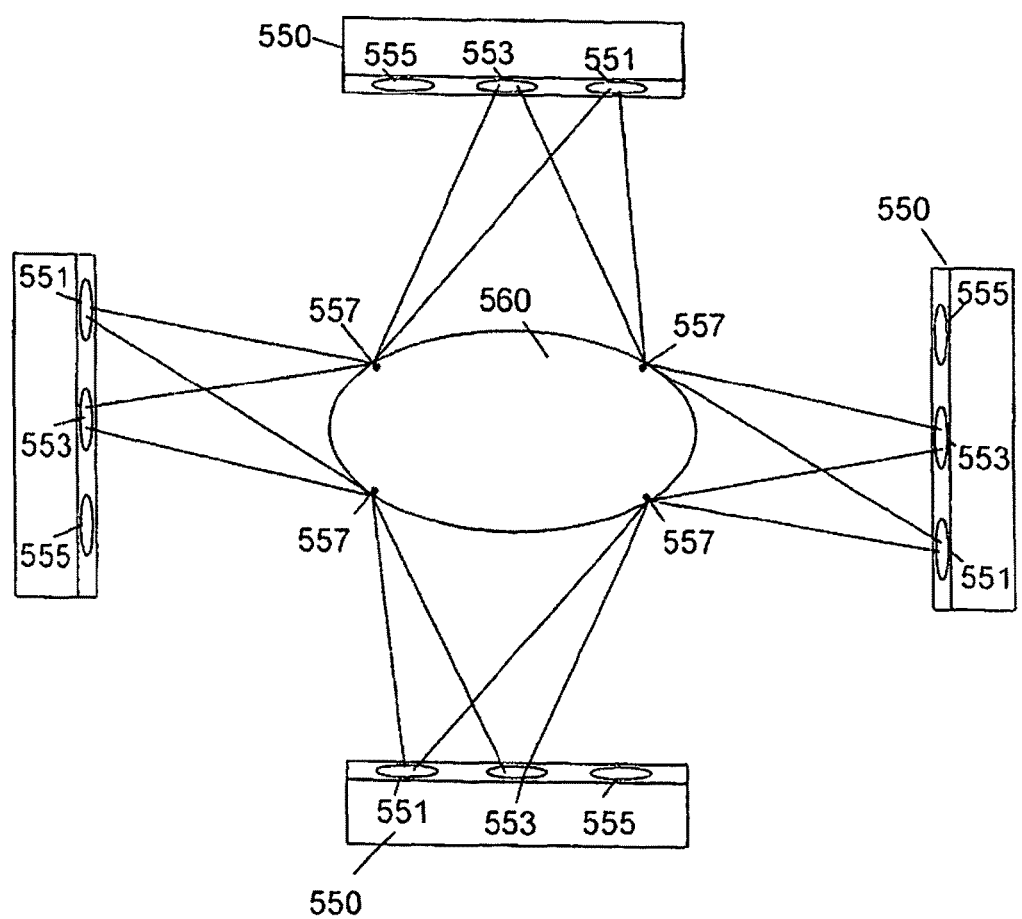

With reference to FIG. 19, in other embodiments the surface data from the optical systems 550 can be combined by using alignment markings 557 on the patient's limb 560. The patient's limb 560 may be covered with a material and a visible or IR marking 557 can be projected onto the patient's limb 560 at locations that are within the field of view of two or more optical systems 550. The color camera 551 may detect both visible and IR markings and the IR camera 553 may only detect IR markings. The optical systems can be able to distinguish the IR light from the IR markings because the shape of the IR marking 557 can be larger or may have a different shape. The surface data from adjacent optical systems 550 can be combined by using a photogrammetry or image correlation process that matches the positions of the markings 557 that are photographed by both optical systems 550.

Figure 20:
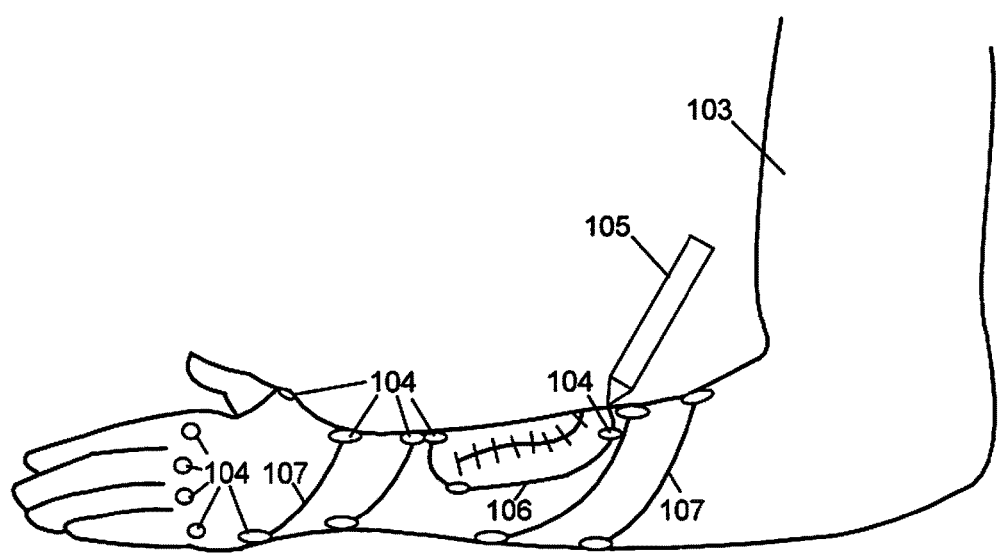
FIG. 20 illustrates a marked patient for detection by the photographic detection system.

In addition to the reference points, the patient can also be marked to define an edge of the brace, a seam of a modular brace or other features. With reference to FIG. 20, the doctor can mark the patient's arm 103 with a pen 105 or with stickers 104 to help define a position of the marker or define the locations of the edge of the brace or identify and locate other important features. The edge marking can be one or more continuous ink lines 107 or stickers 104 that extend around the patient's arm 103. In other embodiments, the edge or other features can be defined by a series of ink marks or stickers 104 that are connected during the brace design. The ink lines 107, stickers 104 or other markings can also be placed on the patient to create visible reference points to indicate areas of interest or brace design points on the patient.

For example, the patient may have injured areas from an operation that has been closed with stitches and should not be in contact with the rigid brace. By providing an opening in the brace, the patient's stitches will not be pressed against the brace structure. In FIG. 20, one or more stickers 104 have been placed on the arm 103 that can be used to detect physical position as described above. The circle 106 or stickers 104 can also be placed around a injured portion of the patient's body so injured portion and position information can be identified by the brace design system and that the brace can be accurately designed around any injured surface areas. Notes or symbols can also be placed on the patient's arm 103. For example, the doctor can write information indicating the location of the injury as well as information indicating the locations of bones, joints, tendons and ligaments. These anatomical locations are important in the design of the brace and are therefore marked on the patient's arm 103. Because photogrammetry uses photographs, the digital pictures will record all stickers 104, lines 107 and other ink markings as well as any visible injuries or light patterns projected onto the arm 103.

In addition to being the proper dimensions, the brace must also be strong enough for the required use. An ankle brace or walking brace may be required to support the user's weight and impact while running or jumping and an arm brace must be able to withstand the normal use forces. In an embodiment, the strength of the brace is determined by the geometry of the brace and the materials used to fabricate the brace. Suitable materials include high strength plastics, such as high strength polyamides, or metals, alloys and composites such as carbon fiber in an epoxy binder.

Figure 21:
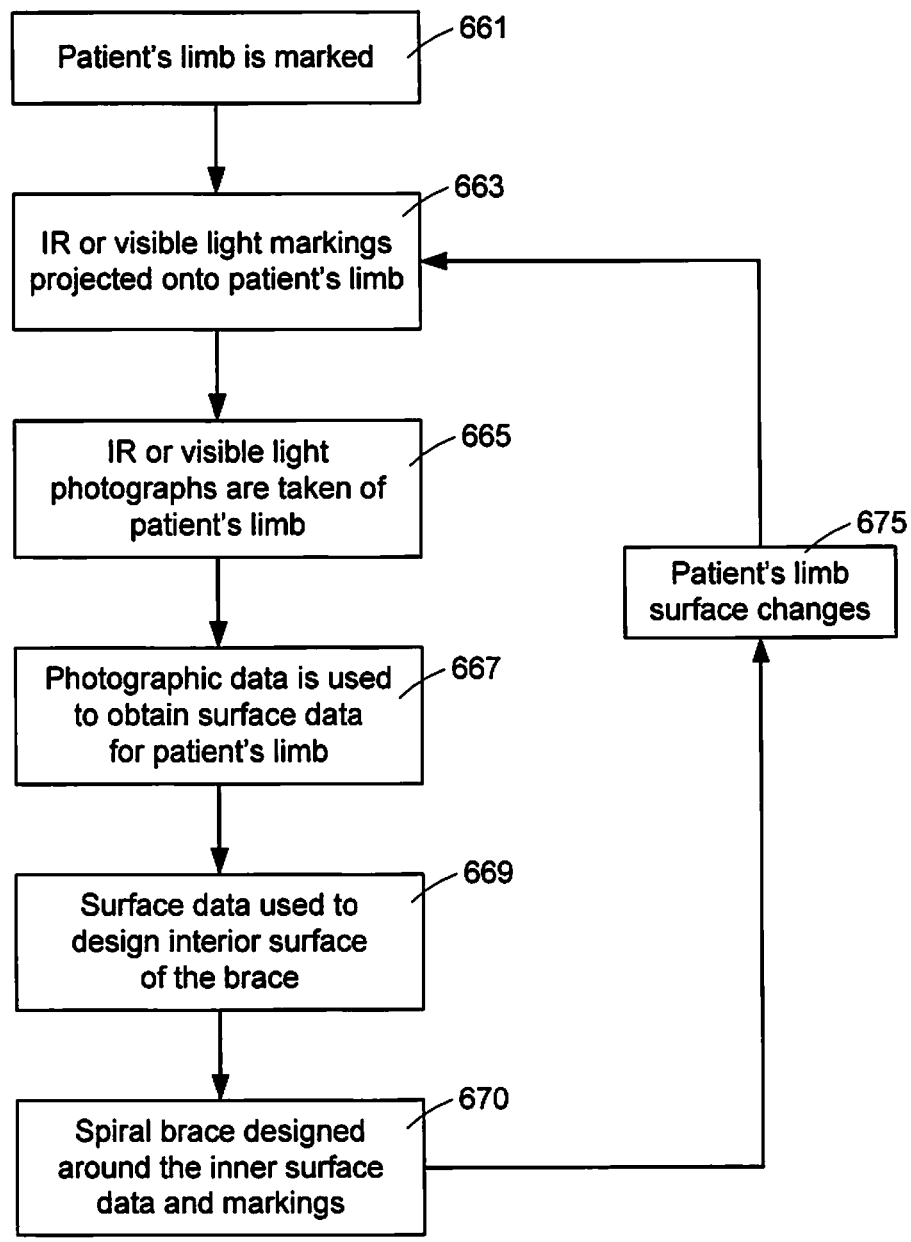
FIG. 21 illustrates a flow chart for fabricating a brace.

With reference to FIG. 21, a flowchart of the process steps for fabricating a brace is illustrated. As discussed above, the patient's limb can be marked 661 with any type of marking device such as a sticker or ink that can be photographed. The markings can indicate a surface location, the location of the injury, edges of the brace, seams of the modular brace, seams of the brace pieces, sensitive areas, locations of stitches, and other body features. The patient's limb can be illuminated with IR or visible light in a pattern such as dots, lines, grids or any other plurality of light points 663. The limb can be photographed with IR and/or visible light cameras 665. From the photographic data, the surface data for the patient's limb can be obtained 667. In other embodiments the limb may not be illuminated with an IR or visible light pattern and the surface data can be obtained by the natural markings on the patient's skin. The surface data can be used to create a digital representation of the limb of the patient.

The surface data or digital representation of the limb of the patient can be used to design interior surfaces of a brace 669. With the limb surface data and additional information about the limb injury, the spiral brace can be designed to prevent specific types of movements and avoid contact with specific areas of the limb 670. In order to provide a comfortable fit, the interior surfaces of the brace can be designed to be slightly larger than the surface data of the limb of the patient and all exposed edges of the brace can have large radii to remove any sharp surfaces. Thus, the interior surface may correspond to the digital representation of the limb of the patient rather than being an exact surface match. If the limb changes in size but remains injured, a new brace may need to be fabricated to provide the required support and restricted movement. The described process can be repeated to fabricate a new brace based upon new photographs of the patient's limb.

After the brace is designed, the brace design data is transmitted to a three dimensional fabrication machine that constructs the brace. In an embodiment, the three dimensional fabrication machine is rapid prototyping, rapid manufacturing, layered manufacturing, 3D printing, laser sintering, and electron beam melting (EBM), fused material deposition (FDM), CNC, etc. The fabrication machine produces a three dimensional single or multiple piece structure that can be plastic, metal or a mix of different materials by forming planar cross section layers of the structure on previously formed planar cross section layers. This layered fabrication process is continued from one end of the structure to the opposite end until the structure is completely fabricated.

In order to efficiently produce the described devices, it can be desirable to simultaneously produce as many component parts as possible. Many fabrication machines can produce parts fitting within a specific volume in a predetermined period of time. For example, a brace can fit around the torso of a patient and have a large space in the center. This brace can be made, but it will only make one device. In order to improve the efficiency, the brace can be designed as multiple pieces that are later coupled or fused together. Rather than making a single brace with the large open center area, the described fabrication methods can be used to simultaneously produce components for two or more braces that occupy the same specific volume as a single piece brace. The cost of fabrication using a three dimensional fabrication machine can be proportional to the amount of time required to print the components rather than the raw material costs. The print time can be minimized by placing as many component cross sections into the print area as possible. If a back or limb brace normally has a large open center area the print cost efficiency can be poor. However, if the brace is a modular design, the modular section pieces can be fabricated in a more efficient manner. For example, multiple modular section pieces can be fabricated simultaneously with the convex surfaces of a first section piece adjacent to concave surfaces of another section piece. By laying out the components in an efficient production manner for fabrication by an additive material machine, the cost of fabrication can be significantly reduced. The components can then be assembled and coupled or fused together to form the brace. In an embodiment, the inner surface of the brace can be manufactured with a high resolution so that the inner surface is very smooth.

When the brace is fabricated using a three dimensional printing machine, the brace is formed by depositing a plurality of parallel planar layers of material with each layer fused to the adjacent layer. Each layer of material used to form the brace can have a predetermined and uniform thickness. In order to optimize the efficiency of the brace fabrication, it can be desirable to minimize the number of parallel planar layers used to create the brace. This minimizes the number of layers that are formed to create the brace and optimizes the fabrication efficiency. In an embodiment, the brace design information can be placed in a virtual box having square corners. The parallel planar layers formed to create the brace can be perpendicular to the shortest dimension of the brace which can be the thickness of the box.

Figure 22:
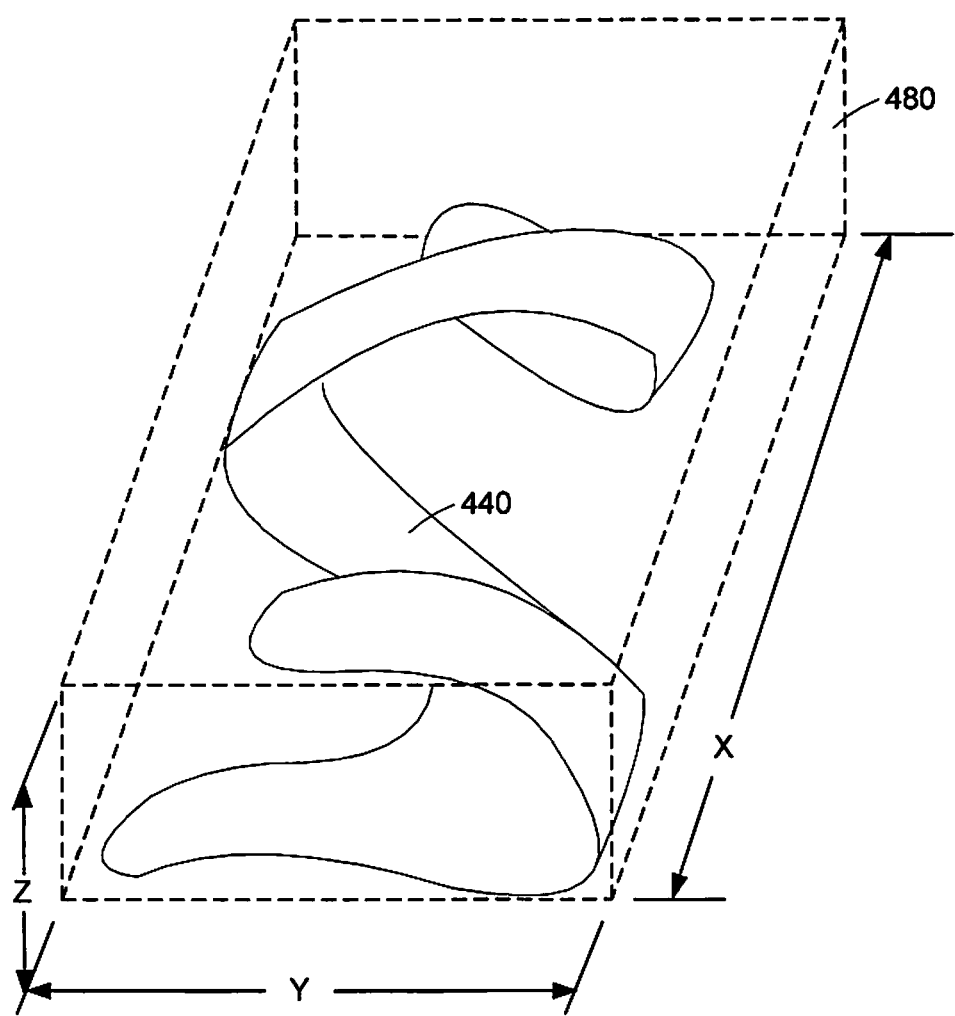
FIG. 22 illustrates an embodiment of the spiral brace design data prior to fabrication with a three dimensional printer.

For example, with reference to FIG. 22, a spiral brace 440 is illustrated in a virtual box 480 having square corners and planar sides. The brace 440 can be an elongated structure that extends from the forearm to the hand and define the length axis. The length of the box 480 X can be the longest dimension of the brace 440 and a thickness of the box 480 Z can be the shortest dimension of the brace 440. In an embodiment, the parallel planar layers that are fused to form the brace 440 can be parallel to the length axis, X. In an embodiment, the parallel planar layers that are fused to form the brace 440 are substantially perpendicular to the thickness axis Z which can be the smallest overall dimension of the brace. In another embodiment, the parallel planar layers that are fused to form the brace 440 are substantially parallel to the width axis Y.

Figure 23:
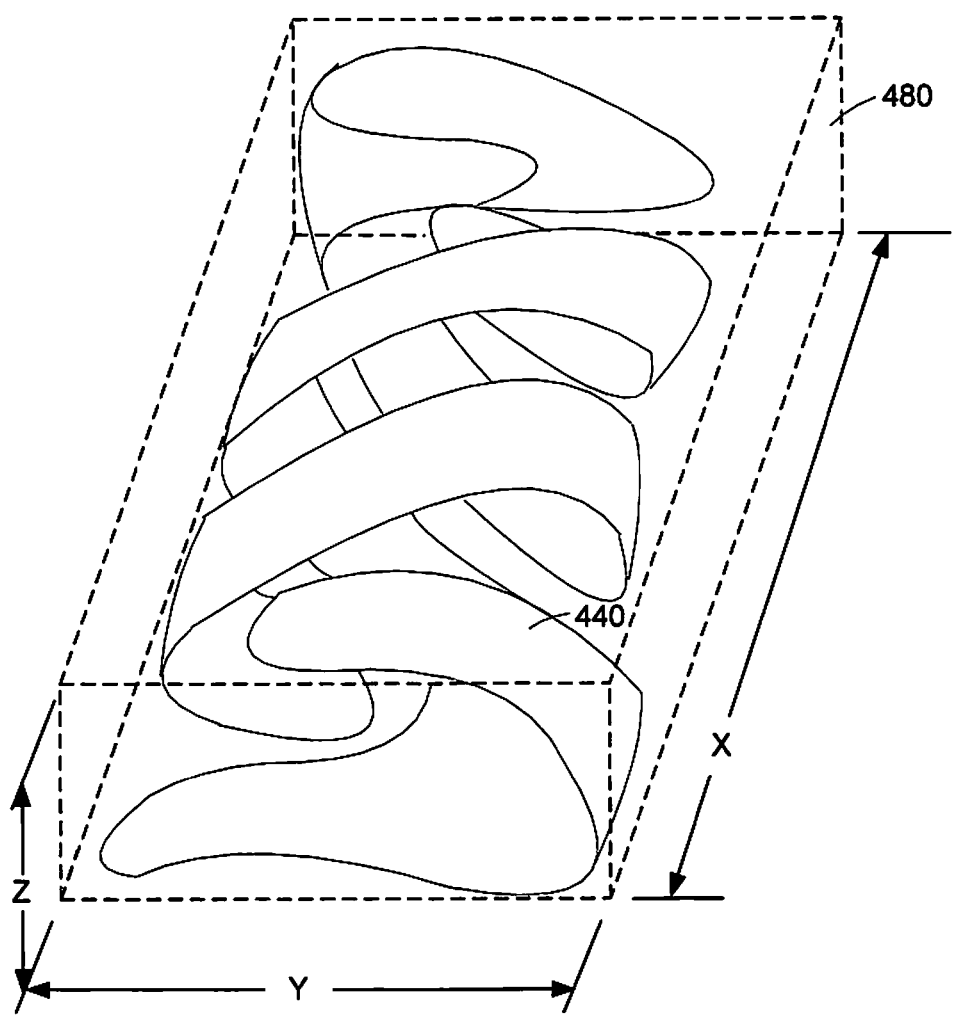
FIG. 23 illustrates an embodiment of the design data for multiple spiral braces prior to fabrication with a three dimensional printer.

In other embodiments, it is possible to further improve the fabrication efficiency. With reference to FIG. 23, a first spiral brace 440 and a second spiral brace 441 are both illustrated in the virtual box 480. In this embodiment, the first spiral brace 440 can be for a first patient and the second spiral brace 441 can be for a second patient. The first spiral brace 440 and the second spiral brace can be arranged in a nested configuration within the virtual box 480. The efficiency of fabrication can be proportional to the number of spiral braces that can be created within a volume. Thus, if two braces can be created in the same virtual box volume, the efficiency of the fabrication is effectively doubled. In other embodiments, it may be possible to include three or more braces within a virtual box volume that is not significantly larger than the virtual box 480.

After the spiral brace has been formed, additional processing can be performed on the inner surface to increase the smoothness. The inner surface can be tumbled, sanded, polished, or other processes can be used to create the smooth inner surfaces of the brace. These processes can be performed by hand or by a machine. In other embodiments, a filler material can be deposited on the inner surface of the brace shell to create a smooth surface. For example, the inner surface may be painted and the paint may fill the uneven surfaces and dry to a smooth surface. Alternatively, the inner surface can be heated to cause the brace material to reflow and create a smooth inner surface.

The use of a photographic process has many advantages over other surface scanning technologies such as laser scanning. The process for transposing the locations of features from the patient to the brace or device is simplified because the doctor can apply location marks to the patient directly or on a form fitting covering. Thus, the locations of the features are much more likely to be accurately placed on the final product. The equipment costs are also reduced because the digital cameras, computers and electronic memory are inexpensive. The photographic equipment is also portable, so it can be easily transported to patient's location. The digital data can then be transmitted electronically to a fabrication machine located at a guild. Alternatively, the digital device data can be recorded onto a disk and transmitted to the fabrication machine.

The present disclosure, in various embodiments, includes components, methods, processes, systems and/or apparatus substantially as depicted and described herein, including various embodiments, subcombinations, and subsets thereof. Those of skill in the art will understand how to make and use the present disclosure after understanding the present disclosure. The present disclosure, in various embodiments, includes providing devices and processes in the absence of items not depicted and/or described herein or in various embodiments hereof, including in the absence of such items as may have been used in previous devices or processes, e.g., for improving performance, achieving ease and/or reducing cost of implementation. Rather, as the following claims reflect, inventive aspects lie in less than all features of any single foregoing disclosed embodiment.

What is claimed is:

1. A custom brace designed to be virtually fitted on a limb of a patient to be braced prior to fabrication for supporting the limb of the patient comprising:
    a brace body having a spiral shape that is adapted to wrap more than one full turn around the limb of the patient, wherein a proximal portion of the brace body is adapted to fit around a forearm portion of the limb, a distal portion of the brace body is adapted to fit around a hand portion of the limb and a thumb section on the distal portion, the thumb section having a thumb hole, the thumb section adapted to surround a thumb of the patient; and
    an inner surface of the brace body that corresponds to a digital representation of the limb of the patient to be braced;
    wherein the brace body has a length axis, the brace body is fabricated in the spiral shape and the brace body in the spiral shape has a plurality of fused planar layers that are parallel to the length axis.

2. The custom brace of claim 1 wherein the distal portion of the brace body has a palmar section that is adapted to support a palm of the hand portion and a dorsal section that is adapted to fit over a dorsum of the hand portion.

3. The custom brace of claim 2 wherein the inner surface of the brace body at the palmar section of the distal portion includes a convex surface.

4. The custom brace of claim 1 wherein each of the fused planar layers of the brace body is made of a homogeneous plastic material that is the same for each of the fused planar layers.

5. The custom brace of claim 1 wherein the distal portion of the brace body is adapted to surround a thumb portion of the limb.

6. The custom brace of claim 1 wherein a width of the brace body at the proximal portion is greater than 0.5 inch and less than 2 inches.

7. The custom brace of claim 1 wherein a thickness of the spiral shape of the brace body is greater than 0.05 inch and less than 0.50 inch.

8. The custom brace of claim 1 wherein a pitch of the spiral shape is greater than 2 inches and less than 6 inches.

9. The custom brace of claim 1 wherein the spiral shape of the brace body defines a center axis and the plurality of fused planar layers are approximately parallel to the center axis.

10. The custom brace of claim 1 wherein the brace body has a single piece spiral configuration.

11. A custom brace designed to be virtually fitted on a limb of a patient to be braced prior to fabrication for supporting an arm of a patient, the arm having fingers, a thumb, a hand, a wrist and a forearm, the custom brace comprising:
    a brace body having a spiral configuration that is adapted to wrap more than one full turn around the arm of the patient to at least partially immobilize the arm of the patient, wherein a proximal portion of the brace body is adapted to fit around the forearm of the arm, a distal portion of the brace body is adapted to fit around the hand of the arm and a thumb section on the distal portion, the thumb section having a thumb hole, the thumb section adapted to surround the thumb of the arm; and
    an inner surface of the brace body that corresponds to a digital representation of the arm of the patient to be braced;
    wherein the brace body has a length axis and the brace body in the spiral configuration has a plurality of fused planar layers that are parallel to the length axis.

12. The custom brace of claim 11 further comprising:
    a distal limb support at a distal end of the brace, the distal limb support is adapted to at least partially surround the hand and not restrict movement of fingers.

13. The custom brace of claim 12 wherein an edge of the distal limb support is adapted to be positioned adjacent to a palmar digital crease of the hand.

14. The custom brace of claim 12 wherein an edge of the distal limb support is adapted to not extend over proximal phalanx segments of the fingers.

15. The custom brace of claim 12 wherein an edge of the distal limb support is adapted to not extend over a thenar portion of the hand allowing a thumb of the hand to move freely.

16. The custom brace of claim 12 wherein the inner surface of the brace body at the distal limb support has a convex surface that is adapted to be adjacent to a palmar surface of the hand.

17. The custom brace of claim 12 wherein the custom brace is adapted to prevent palmar flexion movement of the hand.

18. The custom brace of claim 12 wherein the custom brace is adapted to allow rotational movement of the hand about a center axis of the custom brace relative to the forearm.

19. The custom brace of claim 11 wherein the brace body includes a distal limb support that is adapted to be adjacent to a palmar surface of the hand, a middle section that is adapted to be adjacent to a posterior surface of the wrist and a proximal limb support at a proximal end of the custom brace, the proximal limb support that is adapted to be adjacent to an anterior surface of the forearm.

20. The custom brace of claim 11 wherein the brace body has a single piece spiral configuration.

* * * * *